(12) United States Patent
Bangera et al.

(10) Patent No.: US 9,848,760 B2
(45) Date of Patent: Dec. 26, 2017

(54) DEVICES FOR CONTINUAL MONITORING AND INTRODUCTION OF GASTROINTESTINAL MICROBES

(75) Inventors: Mahalaxmi Gita Bangera, Renton, WA (US); Edward S. Boyden, Cambridge, MA (US); Roderick A. Hyde, Redmond, WA (US); Jordin T. Kare, Seattle, WA (US); Eric C. Leuthardt, St Louis, MO (US); Dennis J. Rivet, Portsmouth, VA (US); Lowell L. Wood, Jr., Bellevue, WA (US)

(73) Assignee: Gearbox, LLC, Bellevue, WA (US)

( * ) Notice: Subject to any disclaimer, the term of this patent is extended or adjusted under 35 U.S.C. 154(b) by 2630 days.

(21) Appl. No.: 12/459,388

(22) Filed: Jun. 29, 2009

(65) Prior Publication Data

US 2010/0331641 A1 Dec. 30, 2010

(51) Int. Cl.
| | |
|---|---|
| *G01N 33/48* | (2006.01) |
| *G01N 33/50* | (2006.01) |
| *A61B 1/04* | (2006.01) |
| *G06F 19/12* | (2011.01) |
| *A61B 5/00* | (2006.01) |
| *G06F 19/00* | (2011.01) |
| *G06F 19/18* | (2011.01) |

(52) U.S. Cl.
CPC ............ *A61B 1/041* (2013.01); *A61B 5/0002* (2013.01); *A61B 5/411* (2013.01); *A61B 5/42* (2013.01); *G06F 19/12* (2013.01); *G06F 19/366* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 5,571,401 A | 11/1996 | Lewis et al. | |
| 5,698,089 A | 12/1997 | Lewis et al. | |
| 6,010,492 A * | 1/2000 | Jacobsen et al. | 604/503 |
| 6,102,892 A | 8/2000 | Putzer et al. | |
| 6,423,884 B1 | 7/2002 | Oehmen | |
| 6,565,847 B1 | 5/2003 | Gorsek | |
| 6,641,808 B1 | 11/2003 | Bojrab | |
| 6,645,530 B1 | 11/2003 | Borody | |
| 6,706,287 B2 | 3/2004 | Ranganathan et al. | |
| 6,712,770 B2 * | 3/2004 | Lin et al. | 600/532 |

(Continued)

FOREIGN PATENT DOCUMENTS

| | | |
|---|---|---|
| EP | 1 397 997 A1 | 3/2004 |
| WO | WO2008/076696 A2 | 6/2008 |
| WO | WO 2008/136769 A1 * | 11/2008 |

OTHER PUBLICATIONS

Bacteria, 2006, two pages. Dictionary of Leisure, Travel, and Tourism. Retrieved online on Oct. 28, 2012 from <<http://www.credoreference.com/entry/acbleisure/bacteria>>.*

(Continued)

*Primary Examiner* — Russell S Negin
(74) *Attorney, Agent, or Firm* — Suiter Swantz pc llo

(57) ABSTRACT

Systems and methods described herein include those for the continual modification of intestinal microbes. Described herein are systems including sampling devices, analysis devices, computational devices and user interface devices as well as methods for the use of such devices in combination.

24 Claims, 17 Drawing Sheets

(56) References Cited

U.S. PATENT DOCUMENTS

| | | |
|---|---|---|
| 7,011,826 B1 | 3/2006 | Rowe et al. |
| 7,211,426 B2 | 5/2007 | Bruessow et al. |
| 7,214,479 B2 | 5/2007 | Welch et al. |
| 7,255,677 B2 | 8/2007 | Burch et al. |
| 7,371,375 B2 | 5/2008 | Zimmer et al. |
| 7,384,778 B2 | 6/2008 | Chen et al. |
| 2003/0167012 A1* | 9/2003 | Friedman et al. ............ 600/506 |
| 2004/0028689 A1 | 2/2004 | Borody |
| 2005/0239706 A1 | 10/2005 | Backhed et al. |
| 2006/0193845 A1 | 8/2006 | Watson et al. |
| 2006/0257991 A1* | 11/2006 | McDevitt et al. ......... 435/287.2 |
| 2007/0104712 A1 | 5/2007 | Ashkenazi et al. |
| 2007/0105791 A1 | 5/2007 | Sears et al. |
| 2007/0123460 A1 | 5/2007 | Chang et al. |
| 2007/0128303 A1 | 6/2007 | Chang et al. |
| 2007/0178078 A1 | 8/2007 | Khoo |
| 2007/0196437 A1 | 8/2007 | Hamaker et al. |
| 2007/0196439 A1 | 8/2007 | Catani et al. |
| 2007/0264636 A1 | 11/2007 | Crosby et al. |
| 2008/0014184 A1 | 1/2008 | Lin et al. |
| 2008/0014185 A1 | 1/2008 | Lin et al. |
| 2008/0102162 A1 | 5/2008 | Delcour et al. |
| 2008/0145451 A1 | 6/2008 | Hageman et al. |
| 2008/0146510 A1 | 6/2008 | Wong et al. |
| 2008/0146609 A1 | 6/2008 | Guiles et al. |
| 2008/0170991 A1 | 7/2008 | Shi et al. |
| 2008/0171376 A1 | 7/2008 | Scholl et al. |
| 2008/0220103 A1 | 9/2008 | Birnbaum et al. |
| 2008/0293997 A1 | 11/2008 | Buhlmann et al. |
| 2009/0092729 A1 | 4/2009 | Sprenger et al. |
| 2009/0112191 A1 | 4/2009 | Boyden et al. |
| 2009/0192449 A1* | 7/2009 | Boyden et al. ................. 604/65 |

OTHER PUBLICATIONS

*Escherichia coli*, 2013, two pages. The Columbia Encyclopedia. Retrieved online on Mar. 18, 2014 from <http://search.credoreference.com>.*

Adlerberth, Ingegerd; "Factors Influencing the Establishment of the Intestinal Microbiota in Infancy"; Nestlè Nutr Workshop Ser Pediatr Program; bearing a date of 2008; pp. 13-33; vol. 62.

Bajzer et al.; "Obesity and gut flora"; Nature, News and Views; bearing a date of Dec. 2006; pp. 1009-1010; vol. 444.

Biolog, Inc.; Biolog Microbial Identification Systems Brochure; Part # 00A002; Rev. A; bearing a date of Jan. 2007; pp. 1-2.

Blandino et al.; "Probiotics: overview of microbiological and immunological characteristics"; Expert Rev. Anti Infect Ther.; bearing a date of 2008; pp. 497-508; vol. 6(4); located at: www.expertreviews.com.

Dibaise et al.; "Gut Microbiota and Its Possible Relationship with Obesity"; Mayo Clin Proc; bearing a date of Apr. 2008; pp. 460-469; vol. 83(4); located at: www.mayclinicproceedings.com.

Dumas et al.; "Metabolic profiling reveals a contribution of gut microbiota to fatty liver phenotype in insulin-resistant mice"; Proc. Natl. Acad. Sci. USA; bearing a date of Aug. 15, 2006; pp. 12511-12516; vol. 103, No. 33; located at: www.pnas.org/cgi/doi/10.1073/pnas.0601056103.

Gomi et al.; "In Vitro Antimicrobial Susceptibility Testing of Bacterial Enteropathogens Causing Traveler's Diarrhea in Four Geographic Regions"; Antimicrobial Agents and Chemotherapy; bearing a date of Jan. 2001; pp. 212-216; vol. 45, No. 1; downloaded from: www.aac.asm.org on Apr. 24, 2009.

Hrdina et al.; "The gastrointestinal microbiota affects the selenium status and selenoprotein expression in mice"; Journal of Nutritional Biochemistry; bearing a date of 2008; pp. 1-11; e-published ahead of print Sep. 30, 2008; available online at www.sciencedirect.com; Elsevier Inc.

Iapichino et al.; "Impact of antibiotics on the gut microbiota of critically ill patients"; Journal of Medical Microbiology; bearing a date of 2008; pp. 1007-1014; vol. 57; Great Britain; located at: http://jmm.sgmjournals.org.

Ivanov et al.; "Specific Microbiota Direct the Differentiation of IL-17-Producing T-Helper Cells in the Mucosa of the Small Intestine"; Cell Host and Microbe; bearing a date of Oct. 16, 2008; pp. 377-349; vol. 4; Elsevier Inc.

Khachatryan et al.; "Predominant Role of Host Genetics in Controlling the Composition of Gut Microbiota"; PLoS ONE; bearing a date of Aug. 26, 2008; pp. 1-16; e3064; vol. 3, No. 8; located at: www.plosone.org.

Leroy et al.; "New insights in the gut microbiota: a key to good health"; Alimentation & Santé: Microbiotica, etc.; bearing a date of Sep. 25, 2008; pp. 1-35.

Ley et al.; "Human gut microbes associated with obesity"; Nature; bearing a date of Dec. 21/28, 2006; pp. 1022-1023; vol. 444.

Li et al.; "Symbiotic gut microbes modulate human metabolic phenotypes"; PNAS-USA; bearing a date of Feb. 12, 2008; pp. 2117-2122; vol. 105, No. 6; located at: www.pnas.org/cgi/doi/10.1073/pnas.0712038105.

Mazmanian et al.; "A microbial symbiosis factor prevents intestinal inflammatory disease"; Nature; bearing a date of May 29, 2008; pp. 620-625; vol. 453.

Napolitano et al.; "Potential prebiotic activity of oligosaccharides obtained by enzymatic conversion of durum wheat insoluble dietary fibre into soluble dietary fibre"; Nutrition, Metabolism & Cardiovascular Diseases; available online as of Sep. 20, 2008; DOI:10.1016/j.numecd.2008.07.005.

Nasidze et al.; "Global Diversity in the Human Salivary Microbiome"; Genome Research; bearing a date of Feb. 27, 2009; pp. 1-8; Cold Spring Harbor Laboratory Press.

Ott et al.; "Quantification of Intestinal Bacterial Populations by Real-Time PCR with a Universal Primer Set and Minor Groove Binder Probes: a Global Approach to the Enteric Flora"; Journal of Clinical Microbiology; bearing a date of Jun. 2004; pp. 2566-2572; vol. 42, No. 6.

Palmer et al.; "Development of the Human Infant Intestinal Microbiota"; PLoS Biology; bearing a date of Jul. 2007; pp. 1556-1573, e177; vol. 5, Issue 7; located at: www.plosbiology.org.

Pathak et al.; "Urea Breath Test for *Helicobacter pylori* Detection: Present Status"; Tropical Gastroenterology; bearing a date of Oct.-Dec. 2004; pp. 156-161; vol. 25, No. 4.

Peltonen et al.; "An Uncooked Vegan Diet Shifts the Profile of Human Fecal Microflora: Computerized Analysis of Direct Stool Sample Gas-Liquid Chromatography Profiles of Bacterial Cellular Fatty Acids"; Applied and Environmental Microbiology; bearing a date of Nov. 1992; pp. 3660-3666; vol. 58, No. 11; American Society for Microbiology.

Penders et al.; "Factors Influencing the Composition of the Intestinal Microbiota in Early Infancy"; Pediatrics; bearing a date of Aug. 2006; pp. 511-521; vol. 118, No. 2: located at: www.pediatrics.org.

Pennisi, Elizabeth; "What Your Spit Says About You"; ScienceNOW Daily News; bearing a date of Feb. 26, 2009; pp. 1-2.

Samuel et al.; "Effects of the gut microbiota on host adiposity are modulated by the short-chain fatty-acid binding G protein-coupled receptor, Gpr41"; PNAS-USA; bearing a date of Oct. 28, 2008; pp. 16767-16772; vol. 105, No. 43; The National Academy of Sciences of the USA.

Scanlan et al.; "Micro-eukaryotic diversity of the human distal gut microbiota: qualitative assessment using culture-dependent and -independent analysis of faeces"; The ISME Journal; bearing a date of 2008; pp. 1-11; International Society for Microbial Ecology.

Schrezenmeir et al.; "Probiotics, prebiotics, and synbiotics—approaching a definition"; The American Journal of Clinical Nutrition; bearing a date of 2001; pp. 361S-364S; vol. 73 (suppl.); American Society for Clinical Nutrition; located at: www.ajcn.org.

Stiefel et al.; "Orally administered β-lactamase enzymes represent a novel strategy to prevent colonization by Clostridium difficile"; Journal of Antimicrobial Chemotherapy; bearing a date of Aug. 7, 2008; pp. 1105-1108; vol. 62; Oxford University Press.

Turnbaugh et al.; "An obesity-associated gut microboime with increased capacity for energy harvest"; Nature; bearing a date of Dec. 21/28, 2006; pp. 1027-1031; vol. 444; Nature Publishing Group.

(56) References Cited

OTHER PUBLICATIONS

Wen et al.; "Innate immunity and intestinal microbiota in the development of Type I diabetes"; Nature; bearing a date of Sep. 21, 2008; pp. 1-6; Macmillan Publishers Limited.
Woodmansey et al.; "Intestinal bacteria and aging"; Journal of Applied Microbiology; bearing a date of 2007; pp. 1178-1186; vol. 102; The Society for Applied Microbiology.
Jiménez et al.; "Is meconium from healthy newborns actually sterile?"; Research in Microbiology; bearing a date of 2008; available online Jan. 11, 2008; pp. 187-193; vol. 159; Elsevier Masson SAS.

\* cited by examiner

FIG. 4

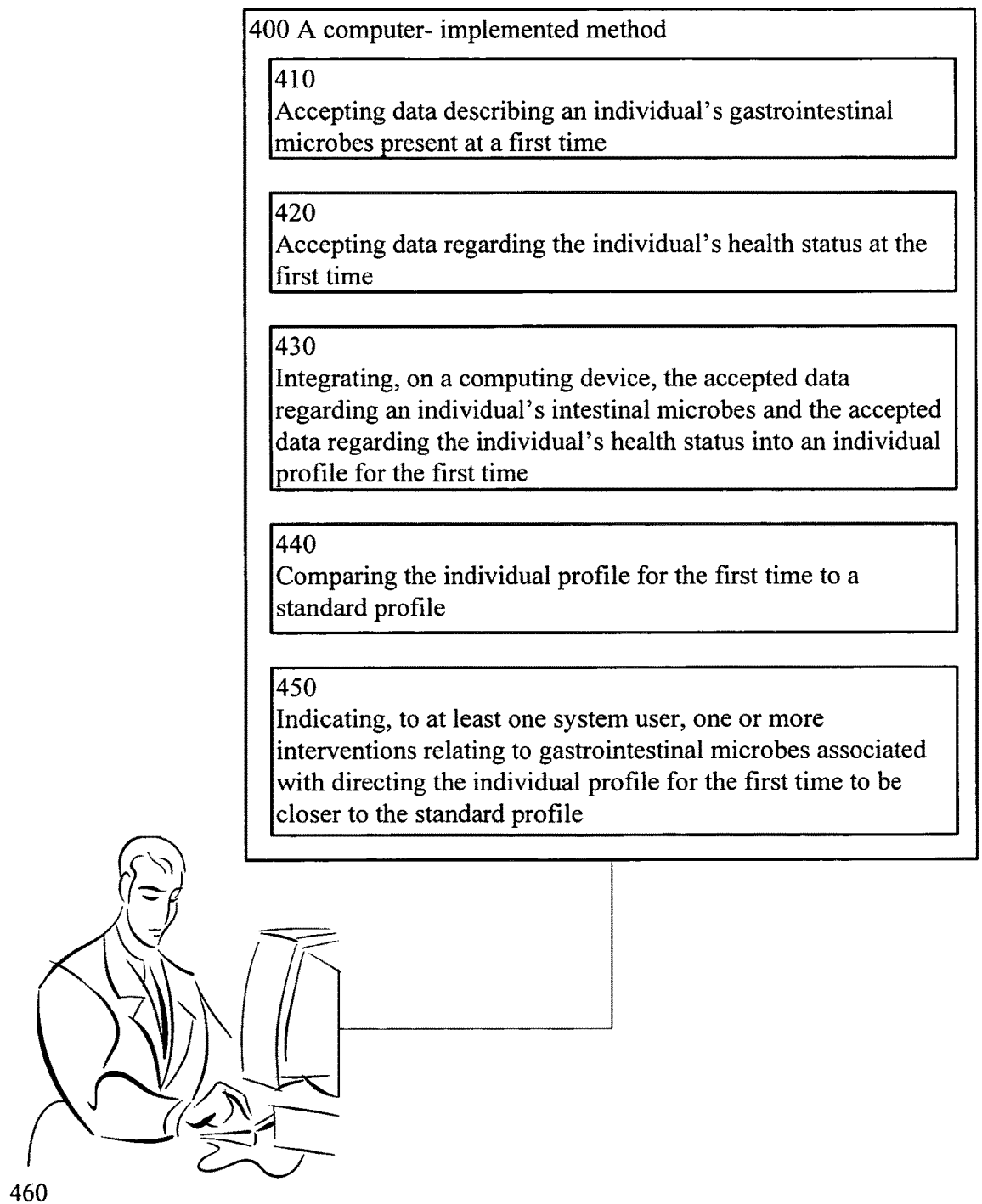

400 A computer-implemented method

410
Accepting data describing an individual's gastrointestinal microbes present at a first time 420
Accepting data regarding the individual's health status at the first time 430
Integrating, on a computing device, the accepted data regarding an individual's intestinal microbes and the accepted data regarding the individual's health status into an individual profile for the first time 440
Comparing the individual profile for the first time to a standard profile 450
Indicating, to at least one system user, one or more interventions relating to gastrointestinal microbes associated with directing the individual profile for the first time to be closer to the standard profile

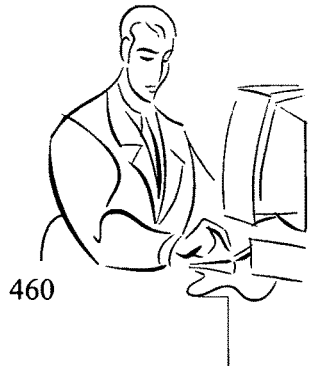

460

400 A computer- implemented method

410
Accepting data describing an individual's gastrointestinal microbes present at a first time 420
Accepting data regarding the individual's health status at the first time 500
Accepting data regarding the individual's diet 510
Accepting data regarding at least one metabolic state of the individual 430
Integrating, on a computing device, the accepted data regading an individual's intestinal microbes and the accepted data regarding the individual's health status into an individual profile for the first time 520
Integrating the accepted data into an individual profile which includes a range of values for the data 440
Comparing the individual profile for the first time to a standard profile 450
Suggesting, to at least one system user, one or more interventions relating to gastrointestinal microbes associated with directing the individual profile for the first time to be closer to the standard profile

FIG. 6

460

400 A computer- implemented method

410
Accepting data describing an individual's gastrointestinal microbes present at a particular time 420
Accepting data regarding the individual's health status at the particular time 430
Integrating, on a computing device, the accepted data regading an individual's intestinal microbes and the accepted data regarding the individual's health status into an individual profile for the particular time 440
Comparing the individual profile for the particular time to a standard profile 450
Suggesting, to at least one system user, one or more interventions relating to gastrointestinal microbes associated with directing the individual profile for the particular time to be closer to the standard profile 600
Signaling for release of one or more gastrointestinal microbe 610
Signaling for release of one or more probiotic agent 620
Associating the individual profile with one or more interventions relating to gastrointestinal microbes to direct the individual profile for the first time to be closer to the standard profile

FIG. 7

460

| 400 A computer- implemented method |
|---|
| 410     Accepting data describing an individual's gastrointestinal microbes present at a particular time |
| 420     Accepting data regarding the individual's health status at the particular time |
| 430     Integrating, on a computing device, the accepted data regading an individual's intestinal microbes and the accepted data regarding the individual's health status into an individual profile for the particular time |
| 440     Comparing the individual profile for the particular time to a standard profile |
| 450     Suggesting, to at least one system user, one or more interventions relating to gastrointestinal microbes associated with directing the individual profile for the particular time to be closer to the standard profile |

700
Accepting data describing an individual's gastrointestinal microbes present at a second time;
Accepting data regarding the individual's health status at the second time;
Integrating, on a computing device, the accepted data regarding an individual's gastrointestinal microbes and the accepted data regarding the individual's health status into an individual profile for the second time;
Comparing the individual profile for the second time to the standard profile; and
Indicating one or more alterations in gastrointestinal microbes associated with directing the individual profile for the second time to be closer to the standard profile 710
Accepting at least one personal parameter relating to the individual; and
Selecting the standard profile to correspond with one or more of the at least one personal parameter

FIG. 8

460

400 A computer-implemented method

410 Accepting data describing an individual's gastrointestinal microbes present at a particular time 420 Accepting data regarding the individual's health status at the particular time 430 Integrating, on a computing device, the accepted data regading an individual's intestinal microbes and the accepted data regarding the individual's health status into an individual profile for the particular time 440 Comparing the individual profile for the particular time to a standard profile 450 Suggesting, to at least one system user, one or more interventions relating to gastrointestinal microbes associated with directing the individual profile for the particular time to be closer to the standard profile 800 Creating, on a computing device, at least one difference listing between the individual profile for the first time and the standard profile;
Associating at least one intervention with minimizing the at least one difference listing; and
Indicating, to at least one system user, at least one intervention associated with minimizing the at least one difference listing 810 Accepting data describing an individual's gastrointestinal microbes present at a second time;
Accepting data regarding the individual's health status at the second time;
Integrating, on a computing device, the accepted data regarding an individual's gastrointestinal microbes and the accepted data regarding the individual's health status into an individual profile for the second time;
Comparing the individual profile for the second time to the individual profile for the first time; and
Indicating to at least one system user at least one difference between the individual profile for the second time and the individual profile for the first time 820 Comparing the individual profile for the second time to the standard profile; and
Indicating to at least one system user at least one difference between the individual profile for the second time and the standard profile

FIG. 9

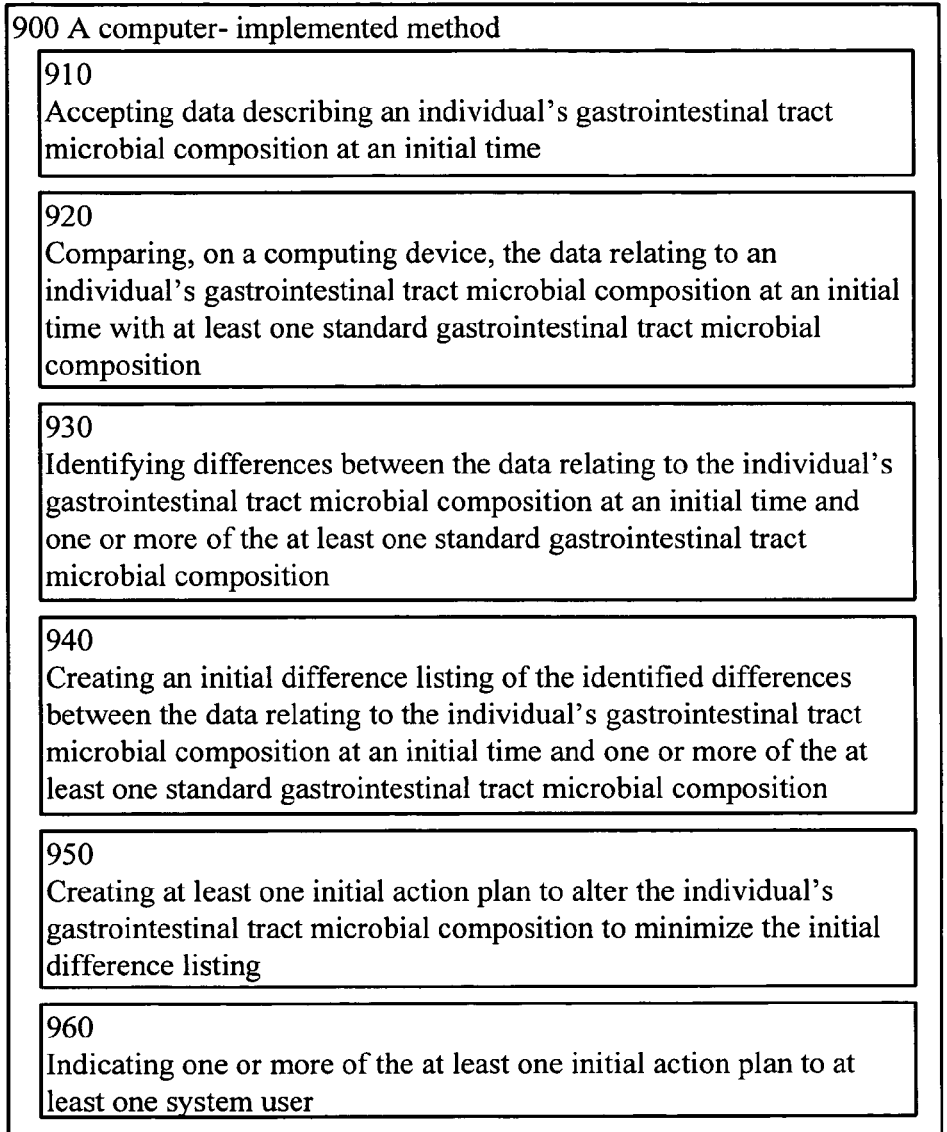

900 A computer- implemented method

910
Accepting data describing an individual's gastrointestinal tract microbial composition at an initial time 920
Comparing, on a computing device, the data relating to an individual's gastrointestinal tract microbial composition at an initial time with at least one standard gastrointestinal tract microbial composition 930
Identifying differences between the data relating to the individual's gastrointestinal tract microbial composition at an initial time and one or more of the at least one standard gastrointestinal tract microbial composition 940
Creating an initial difference listing of the identified differences between the data relating to the individual's gastrointestinal tract microbial composition at an initial time and one or more of the at least one standard gastrointestinal tract microbial composition 950
Creating at least one initial action plan to alter the individual's gastrointestinal tract microbial composition to minimize the initial difference listing 960
Indicating one or more of the at least one initial action plan to at least one system user

970

900 A computer- implemented method

910 Accepting data describing an individual's gastrointestinal microbes present at an initial time 920 Comparing, on a computing device, the data relating to an individual's gastrointestinal tract microbial composition at an initial time with at least one standard gastrointestinal tract microbial composition 930 Identifying differences between the data relating to the individual's gastrointestinal tract microbial composition at an initial time and one or more of the at least one standard gastrointestinal tract microbial composition 940 Creating an initial difference listing of the identified differences between the data relating to the individual's gastrointestinal tract microbial composition at an initial time and one or more of the at least one standard gastrointestinal tract microbial composition 950 Creating at least one initial action plan to alter the individual's gastrointestinal tract microbial composition to minimize the initial difference listing 1000 Wherein the at least one initial action plan comprises one or more dietary suggestions 960 Indicating one or more of the at least one initial action plan to at least one system user 1010 Accepting data relating to an individual's gastrointestinal tract microbial composition at a second time;
Comparing, on a computing device, the data relating to an individual's gastrointestinal tract microbial composition at a second time with the initial difference listing;
Creating a second difference listing;
Creating at least one second action plan to alter the individual's gastrointestinal tract microbial composition; and
Suggesting one or more of the at least one second action plan to the system user

FIG. 11

970

900 A computer-implemented method

910   Accepting data describing an individual's gastrointestinal microbes present at an initial time 920   Comparing, on a computing device, the data relating to an individual's gastrointestinal tract microbial composition at an initial time with at least one standard gastrointestinal tract microbial composition 930   Identifying differences between the data relating to the individual's gastrointestinal tract microbial composition at an initial time and one or more of the at least one standard gastrointestinal tract microbial composition 940   Creating an initial difference listing of the identified differences between the data relating to the individual's gastrointestinal tract microbial composition at an initial time and one or more of the at least one standard gastrointestinal tract microbial composition 950   Creating at least one initial action plan to alter the individual's gastrointestinal tract microbial composition to minimize the initial difference listing 960   Indicating one or more of the at least one initial action plan to at least one system user 1100   Accepting data relating to the individual's personal history; and Selecting one or more of the at least one standard gastrointestinal tract microbial composition in relation to the individual's personal history 1110   Accepting data regarding at least one personal parameter of the individual; Creating an action plan in relation to the accepted data regarding the at least one personal parameter of the individual; and Indicating the action plan in relation to the accepted data regarding the at least one personal parameter of the individual to a system user 1120   Signaling at least some portion of the indicated one or more action plans to one or more dispenser

FIG. 13

|  | Bifidobacteria | | E coli | | C difficile | |
| --- | --- | --- | --- | --- | --- | --- |
|  | Coefficient (P) | OR (99% CI) | Coefficient (P) | OR (99% CI) | Coefficient (P) | OR (99% CI) |
| Cesarean section (compared with vaginal delivery) | −0.34 (.003)[a] | ND | 0.07 (.677) | 1.04 (0.38–2.83) | 0.88 (.24) | 2.07 (1.01–4.25)[a] |
| Hospitalization (d) | −0.01 (.365) | ND | 0.04 (.108) | 1.00 (0.86–1.17) | 0.06 (.364) | 1.13 (1.01–1.25)[a] |
| Prematurity (compared with term infants) | 0.38 (.282) | ND | −0.81 (.109) | 0.11 (0.01–1.15) | 2.83 (.007)[a] | 4.47 (0.48–41.85) |
| Exclusive formula-fed (compared with exclusively breastfed) | −0.10 (.233) | ND | 0.24 (.031) | 2.90 (1.22–6.89)[a] | 1.03 (.003)[a] | 1.88 (1.13–3.11)[a] |
| Antibiotic use by infant (yes/no) | −0.66 (.001)[a] | ND | 0.06 (.825) | 0.57 (0.12–2.66) | 0.94 (.324) | 0.59 (0.13–2.75) |
| Miconazole use by infant (yes/no) | −0.59 (.003)[a] | ND | 0.41 (.142) | 0.60 (0.13–2.90) | 0.04 (.965) | 1.01 (0.25–4.09) |
| Siblings (yes/no) | 0.25 (.001)[a] | ND | 0.21 (<.025) | 1.45 (0.82–2.57) | −0.32 (.277) | 1.01 (0.66–1.56) |

FIG. 16

| Bacterial Taxa | Control | Remission | Attack |
|---|---|---|---|
| Class Gammaproteobacteria * | 0.2% | 2.1% | 0% |
| Order Enterobacteriales * | 0% | 1.6% | 0% |
| Family Enterobacteriaceae * | 0% | 1.6% | 0% |
| Family Acidaminococcaceae*,*** | 9.2% | 14.8% | 3.1% |
| Family Prevotellaceae ** | 28.8% | 24.5% | 17.3% |
| Family Porphyromonadaceae**,*** | 2.3% | 3.3% | 9.4% |
| Genus Ruminococcus * | 0.2% | 2.8% | 1.6% |
| Genus Roseburia * | 2.8% | 0.8% | 2.4% |
| Genus Megasphaera*,*** | 0.2% | 4.5% | 0% |
| Genus Dialister**,*** | 7.9% | 6.7% | 0% |
| Genus Phascolarctobacterium ** | 0% | 0.6% | 3.1% |
| Genus Faecalibacterium**,*** | 6.5% | 6.5% | 14.2% |
| Genus Prevotella ** | 28.4% | 23.1% | 16.5% |
| Genus Parabacteroides**,*** | 1.2% | 2.1% | 5.9% |

FIG. 17

| Antimicrobial | $MIC_{90}$ (µg/ml)[e] (no. of strains) | | | | | |
|---|---|---|---|---|---|---|
| | ETEC (97) | EAEC (75) | Salmonella (46) | Shigella (36) | Campylobacter (9) | Others[c] (21) |
| AMP | >1,024 | >1,024 | 4 | 512 | 64 | 512 |
| DOX | 64 | 64 | 128 | 128 | 64 | 4 |
| NAL | 256 | 128 | 16 | 8 | 4 | 32 |
| TMP | 1,024 | >1,024 | 1,024 | 1,024 | 64 | 128 |
| SXT | >1,024 | >1,024 | 512 | >1,024 | 128 | 4 |
| CRO[b] | ≤0.0156 | 0.0312 | 0.125 | 0.0312 | 2 | NA |
| MEC | 8 | 16 | 2 | 16 | 4 | 1 |
| CIP | 0.25 | 0.25 | 0.0312 | 0.0312 | 0.0625 | ≤0.0156 |
| LVX | 1 | 1 | 0.25 | 0.25 | 0.25 | 0.0625 |
| AZM[b] | ≤0.0156 | ≤0.0156 | 1 | 0.5 | 0.25 | NA |
| RFX | 32 | 32 | 64 | 64 | 32 | 4 |

DEVICES FOR CONTINUAL MONITORING AND INTRODUCTION OF GASTROINTESTINAL MICROBES

SUMMARY

In one aspect, a system includes but is not limited to a system for continual modification of intestinal microbes including a set of devices. The devices include: at least one sampling device operable for taking at least one sample of an individual's gastrointestinal microbes; at least one analysis device operable for analysis of the at least one sample; at least one computational device operable for accepting data regarding the analysis of the at least one sample and comparing the data to a standard profile; and at least one user interface device operably connected to the at least one computational device. In one aspect, a system includes but is not limited to a system for monitoring and introducing gastrointestinal microbes into a mammalian gastrointestinal tract over time, including a set of devices. The devices include: at least one gastrointestinal microbe analysis device; at least one computational device; at least one user interface operably connected to the at least one computational device; and at least one dispenser operably connected to the at least one computational device. In addition to the foregoing, other system aspects are described in the claims, drawings, and text forming a part of the present disclosure.

In an aspect, a method includes but is not limited to a computer-implemented method including: accepting data describing at least one aspect of an individual's gastrointestinal microbes present at a particular time; accepting data regarding at least one aspect of the individual's health status at the particular time; integrating, on a computing device, the accepted data regarding the individual's gastrointestinal microbes and the accepted data regarding the individual's health status into an individual profile for the particular time; comparing the individual profile for the particular time to a standard profile; and indicating, to at least one system user, one or more interventions relating to gastrointestinal microbes associated with directing the individual profile for the particular time to approximate the standard profile. In one aspect, a method includes but is not limited to a computer-implemented method for suggesting adjustments to gastrointestinal microbe profiles over time, including: accepting data relating to at least one aspect of an individual's gastrointestinal tract microbial composition at an initial time; comparing, on a computing device, the data relating to at least one aspect of an individual's gastrointestinal tract microbial composition at an initial time to at least one standard gastrointestinal tract microbial composition; identifying differences, if any, between the data relating to the at least one aspect of the individual's gastrointestinal tract microbial composition at an initial time and one or more of the at least one standard gastrointestinal tract microbial composition; creating an initial difference listing of the identified differences between the data relating to the individual's gastrointestinal tract microbial composition at an initial time and one or more of the at least one standard gastrointestinal tract microbial composition; creating at least one initial action plan to alter at least one aspect of the individual's gastrointestinal tract microbial composition to minimize the initial difference listing; and indicating one or more of the at least one initial action plan to at least one system user. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4 is a flowchart of a computer-implemented method.

FIG. 5 depicts alternate embodiments of the method shown in FIG. 4.

FIG. 6 shows alternate embodiments of the method shown in FIG. 4.

FIG. 7 illustrates alternate embodiments of the method shown in FIG. 4.

FIG. 8 is a flowchart of a computer-implemented method.

FIG. 9 depicts alternate embodiments of the method shown in FIG. 8.

FIG. 10 illustrates alternate embodiments of the method shown in FIG. 8.

FIG. 11 illustrates alternate embodiments of the method shown in FIG. 8.

FIG. 13 depicts linear regression coefficients for bacterial counts and odds ratios for the presence of gut bacteria, with respect to determinants in multivariate analyses.

FIG. 16 illustrates the comparison of 16S rRNA gene libraries derived from healthy controls and FMF patients in remission and attack.

FIG. 17 depicts minimum inhibitory concentrations (MIC) of antimicrobials for a list of enteropathogens.

DETAILED DESCRIPTION

Figure 1:
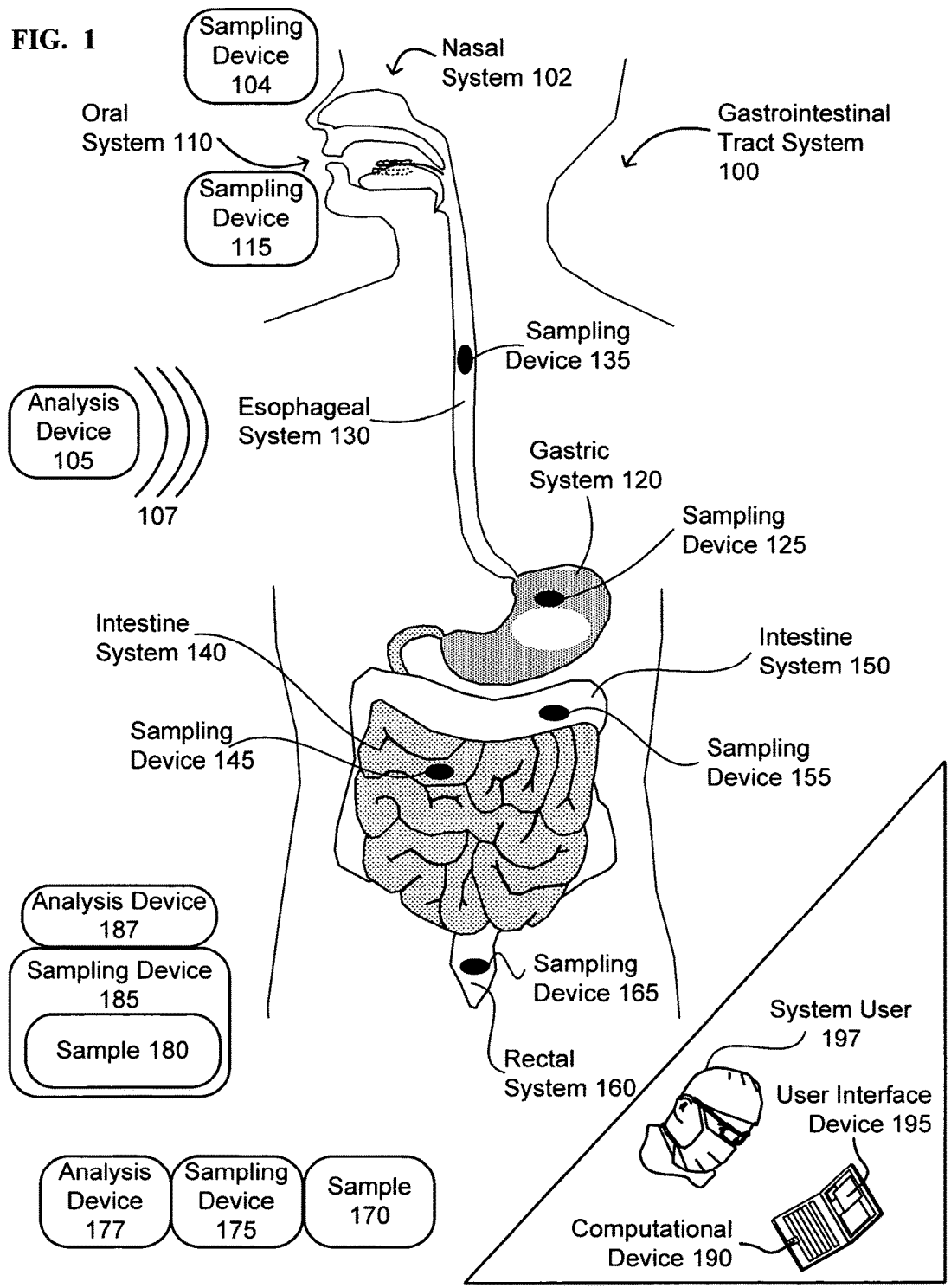
FIG. 1 is a schematic of a system including multiple devices.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Aspects of the systems and methods described herein are illustrated in FIG. 1. Systems and methods as described herein are intended for use in relation with the mammalian gastrointestinal tract system. As an overview, the mammalian gastrointestinal tract system 100 includes multiple sub-systems, such as the nasal system 102, oral system 110, esophageal system 130, gastric system 120, small and large intestine systems 140 and 150, and rectal system 160. In some contexts as used herein the small and large intestine systems 140, 150 will be described collectively as the intestine system. Although a human gastrointestinal tract system is depicted in FIG. 1, in some embodiments the methods and systems described herein may be used with other mammals, such as domesticated animals, for example cats, dogs, cattle, pigs, horses, sheep or goats. Normally in mammals microbial populations reside within all sub-systems of the gastrointestinal tract system. As used herein, "microbe" includes one or more species or strain of microscopic agents from the three domains eubacteria, eukarya and archaea as well as viruses. For example, the oral system, which includes structures such as the mouth, tongue, teeth, oral cavity and salivary glands, hosts a varied microbial population. For example, in humans microbes from saliva have been shown to be diverse between individuals, with each individual's oral cavity hosting multiple bacterial genera. See Nasidze et al., "Global Diversity in the Human Salivary Microbiome," Genome Research published online Feb. 27, 2009, and ScienceNOW Daily News "What your spit says about you," 26 Feb. 2009, each of which is incorporated herein by reference. For example, the gastrointestinal microbes of an individual have been demonstrated to adapt and change over time, see Adlerberth, "Factors influencing the establishment of the intestinal microbiota in infancy," Nestle Nutr Workshop Ser Pediatr Program, 62:13-33 (2008), which is herein incorporated by reference. For example, the intestine system 140, 150 and the rectal system 160 host an array of prokaryotic and eukaryotic diversity both within and between individuals. See Scanlan and Marchesi, "Micro-eukaryotic diversity of the human distal gut microbiota: qualitative assessment using culture-dependent and -independent analysis of faeces," The ISME Journal, 1-11 (2008), which is herein incorporated by reference. Within a given individual at a particular time, there may be a mixture of microbes in each region of the gastrointestinal tract and the mixtures may have some overlap between regions. For example, in some instances, microbes from the nasal system may pass into the oral system or other regions of the gastrointestinal system, for example during sneezing or coughing. For example, microbes from the nasal system or the oral system may pass into other portions of the gastrointestinal system through swallowing or the normal flow of matter during digestion. Generally, microbial populations would tend to move through the entirety of the gastrointestinal system from the oral system through to the rectal system due to normal physiological action of an individual body. Although the same microbes are unlikely to colonize every portion of the gastrointestinal system in an individual, microbes that colonize other regions may be present in a given region through routine physiological activity.

The specific types and relative quantities of microbes present in an individual's gastrointestinal system have been linked to the health and well-being of the individual. As used herein, a group of microbes, or a microbial population, taken as a whole is referred to as a "microbiota," and when the group is quantitated or measured in some manner it is referred to as a "microbiome." However these terms may be used interchangeably in some contexts, as a microbiome is often taken as representative of a microbiota. For example, the microbes present in an individual's gastrointestinal system, taken as a whole, constitute that individual's "gut microbiota." A balanced gut microbiota is required for intestinal health, and there is an emerging view that specific diseases are characterized by specific gut microbiota imbalances, see for example the slides of Leroy and De Vuyst, titled "New insights in the gut microbiota: a key to good health," from Alimentation & Sante: Microbiotica, etc. in Liege, Sep. 25, 2008, which is herein incorporated by reference. For example, some microbes have been associated with differential daily requirements of nutrients, see Hrdina et al., "The gastrointestinal microbiota affects the selenium status and selenoprotein expression in mice," Journal of Nutritional Biochemistry, available online 30 Sep. 2008, which is herein incorporated by reference. For example, some microbes have been linked to obesity, see DiBaise et al., "Gut microbiota and its possible relationship with obesity," Mayo Clin Proc 83(4):460-469 (2008), and Turnbaugh et al., "An obesity-associated gut microbiome with increased capacity for energy harvest," Nature 444: 1027-1031 (2006), which are herein incorporated by reference. It has been suggested that the relative levels of some microbial species in the gastrointestinal system may be manipulated as an approach to obesity; see Ley et al., "Human gut microbes associated with obesity," Nature 444:1022-1023, (2006), and Bajzer and Seeley, "Obesity and gut flora," Nature News and Views 444: 1009-1010 (2006), and WO 2008076696 titled "The gut microbiome as a biomarker and therapeutic target for treating obesity or an obesity-related disorder," which are herein incorporated by reference. Genetic factors of an individual also affect the microbial population in the individual's gastrointestinal system, see for example Khachatryan et al., "Predominant role of host genetics in controlling the composition of gut microbiota," PLoS ONE, 3:e3064 (2008), which is herein incorporated by reference. More specifically, the activity of proteins and other metabolites in individual hosts have been shown to be affected by the presence of some species of microbes in the gut, see Samuel et al., "Effects of the gut microbiota on host adiposity are modulated by the short-chain fatty acid binding G protein-coupled receptor, Gpr41," PNAS-USA 105(43): 16767-16772 (2008), which is incorporated herein by reference. Although the gastrointestinal system microbial population is complex, it has been suggested that key functional members of the microbiome most influence host metabolism and thus health, a concept which has been termed "functional metagenomics," see for example Li et al., "Symbiotic gut microbes modulate human metabolic phenotypes," PNAS-USA, 105(6):2117-2122 (2008), which is incorporated herein by reference. For example, certain molecules of the bacterial microbiota have been indicated as protective for inflammatory bowel disease (IBD), see Mazmanian "A microbial symbiosis factor prevents intestinal inflammatory disease," Nature 453: 620-625 (2008), which is herein incorporated by reference. For example, interaction of gastrointestinal microbes with an individual's immune system have been suggested to be a critical epigenetic factor modifying type I diabetes predisposition, see Wen et al., "Innate immunity and intestinal microbiota in the development of Type I diabetes," Nature 455: 1109-1113 (2008), which is incorporated herein by reference.

Systems described herein include devices operable for sampling microbial populations from regions of the gastrointestinal system. In some embodiments, the sampling device is configured to directly sample the microbial population in a region, while in others the sampling device is configured to sample a product of the microbes, such as metabolic waste products or cellular debris of the microbial population. In some embodiments, the sampling devices operate internally to the body, including one or more sampling device 104 for the nasal system 102, one or more sampling device 115 for the oral system 110, one or more sampling device 135 for the esophageal system 130, one or more sampling device 125 for the gastric system 120, one or more sampling device 145, 155 for the intestine system 140, 150 and one or more sampling device 165 for the rectal system 160. For example, one or more sampling device 104 for the nasal system 102 may include one or more sampling device that is configured to operate after being placed in the upper nasal passages, nose, or in the back of the throat in the lower nasal passages. For example, an endoscopy instrument may be placed in the nasal system and used to sample mucus or tissue. For example, an elongated swab or similar object may be placed in the nasal system and used to sample mucus or tissue. For example, one or more sampling device 115 for the oral system 110 may include one or more sampling device that is configured to be operable after being placed into the oral cavity. Examples of sampling devices for the oral system include, but are not limited to, absorbent pads, tubes for collection of salivary fluid, and scrapings from the interior of the mouth. In some instances, a specialized device for sampling the oral system may be implemented such as described in European Patent Application Publication EP1397997 to Groschl and Rauh, titled "Detection Device," which is herein incorporated by reference. For example, one or more sampling device 115 for the oral system 110 may include a device that is configured to sample breath. See, for example, U.S. Pat. No. 7,255,677 to Burch et al., titled "Detection, diagnosis and monitoring of a medical condition or disease with artificial olfactometry," which is herein incorporated by reference. For example, one or more sampling device 115 for the oral system 110, one or more sampling device 135 for the esophageal system 130, one or more sampling device 125 for the gastric system 120, one or more sampling device 145, 155 for the intestine system 140, 150 and one or more sampling device 165 for the rectal system 160 may include one or more sampling device that is operable after being swallowed and passed through the gastrointestinal tract system 100 during the operation of an individual's gastrointestinal physiology. See, for example, U.S. patent application to Boyden et al., titled "Adaptive dispensation in a digestive tract," filed on Oct. 23, 2007 and US Patent Application No. 2009/0112191 to Boyden et al. titled "Medical or veterinary digestive tract utilization systems and methods" which are herein incorporated by reference. For example, one or more sampling device 135 for the esophageal system 130 may include a tethering component, and configured to be withdrawn through the mouth at an appropriate time point after being swallowed or inserted into the esophagus. For example, a sampling device for the esophageal system may include an endoscopy device. For example, one or more sampling device 165 for the intestinal system or rectal system 160 may be configured to be inserted anally. In some embodiments, sampling devices operate externally to an individual's body, 175, 185. For example, sampling devices 175, 185 may retain gastrointestinal tract samples external to the body. For example, sampling devices may retain salivary fluid, mucus, vomit, intestinal matter, or fecal matter collected after exit from an individual body.

The types and targeted locations of sampling devices in a particular embodiment may depend on, for example, user preference, cost, accuracy, comfort of the individual, safety, speed, duration or durability. The types and targeted locations of sampling devices may also depend on what species of mammal the system is intended for use with. For example, when sampling from human infants, fecal matter may be easily obtainable with minimal invasion. Or example, in individuals undergoing routine endoscopy, tissue and mucus may be sampled as part of the endoscopy process with minimal additional discomfort and inconvenience to the individual. For example, when sampling from domesticated animals, salivary fluid may be obtainable during routine daily animal care, such as during cleaning or feeding, or fecal matter may be obtainable from a stall, box or cage. Various sampling devices implemented together or singly are envisioned for use in different embodiments. Some systems may include sampling devices configured to operate in a single organ system while others may include sampling devices configured to operate in two or more organ systems. For example, an oral system 110 sampling device 115 may be used in addition to or in conjunction with a gastric system 120 sampling device 125. In some aspects, a sampling device may obtain samples from more than one organ system. For example, an ingestible sampling device may sample from multiple locations, such as the oral system 110, esophageal system 130, intestine system 140, 150 and rectal system 160 as it moves through the gastrointestinal tract system 100 as part of an individual's physiological processes. See, for example, U.S. patent application to Boyden et al., titled "Adaptive dispensation in a digestive tract, filed on Oct. 23, 2007 and US Patent Application No. 2009/0112191 to Boyden et al. titled "Medical or veterinary digestive tract utilization systems and methods" which are herein incorporated by reference. For example, a sampling device may include a tethering mechanism for the withdrawal of the sampling device after passing through more than one region of the gastrointestinal tract system 100, such as a sampling device that is placed in the mouth to sample the oral system 110 before being swallowed and thereafter sampling the esophageal system 130 before retraction and removal from the gastrointestinal tract system 100. In some systems, multiple sampling devices targeting a single system may be included. For example, two or more oral system 110 sampling devices 115 may be implemented at the same time or in series.

It is envisioned that the systems as described herein will be used to take multiple samples from the gastrointestinal system of an individual over time. In some embodiments, the systems as described herein may be configured to operate continually, or repeatedly with time breaks in between samples being taken. For example, systems as described herein may operate over a period of days, with sampling devices operating daily, every other day, or in periodic intervals of days. For example, systems as described herein may be implemented to take samples from an individual weekly or monthly. It may be desirable in some situations to monitor an individual in shorter intervals for some time period followed by longer intervals between samples being taken. In some situations, sampling may occur on a schedule set by other events, such as medical testing, routine care, or accessibility of an individual. For example, a domestic animal may be easily sampled during daily routines such as feeding or cleaning. In some embodiments, sampling from the gastrointestinal system of an individual over time may be implemented through the use of multiple single use sampling devices. In some embodiments, sampling from the gastrointestinal system of an individual over time may be implemented through the use of a sampling device that may be used more than once, for example a sampling device that may be recharged, refurbished or reused. In some embodiments, sampling from the gastrointestinal system of an individual over time may be implemented through the use of a sampling device that may be ingested and durably persist in the gastrointestinal tract of an individual, with sufficient time to take multiple samples before the device leaves the individual's gastrointestinal system.

As all regions and sub-systems of the gastrointestinal tract system 100 normally contain microbes, in various embodiments the types of samples retained by the one or more sampling devices 104, 115, 135, 125, 145, 155, 165, 175 and 185 may include samples from all regions and sub-systems of the gastrointestinal tract system 100. The types of samples retained by the one or more sampling devices may be tissue, secretory or waste product samples of the gastrointestinal system 100. Such samples would be analyzed as described herein to yield information relating to the microbial composition of regions or sub-systems of the gastrointestinal tract system 100, or the gastrointestinal tract system 100 generally. For example, one or more samples may include breath. For example, one or more samples may include mucus secretions from the nasal system 102. For example, one or more samples may include salivary fluid from the oral system 110, or the esophageal system 130. For example, one or more samples may include mucus secretions from the esophageal system 130. For example, one or more samples may include gastric fluid from the gastric system 120. For example, one or more samples may include intestinal contents from the intestine system 140, 150. For example, one or more samples may include fecal matter from the rectal system 160. In some embodiments, the samples may also include tissue from the gastrointestinal tract system 100 wherein the tissue contains a microbial population as part of its cellular structure or secretions. Samples may also include tissue or cell debris that has been sloughed off or removed from the surface of the gastrointestinal tract system 100, such as intestinal tissue or cell debris that has sloughed off during physiological processes, or cell debris that has been scraped off by a sampling device, such as during oral or nasal sampling with swabs or endoscopy of any portion of the gastrointestinal system.

Sampling devices that would be suitable for implementation in the systems as described herein include passive devices that enclose, attach or support a sample. Examples include containers, sampling swabs or sticks, and absorbent pads which may be used as sampling devices for mucus, secretions, salivary fluids or fecal matter. In some embodiments, samples may be retained internally to the sampling device, such as diagrammed by sample 180 and sampling device 185 in FIG. 1. For example, a sampling device may include a cup, reservoir, indentation, receptacle, tank or other form of storage internal to the sampling device. See, for example, European Patent Application Publication EP1397997 to Groschl and Rauh, titled "Detection Device," which is herein incorporated by reference. In some embodiments, samples may be retained externally to the sampling device, such as diagrammed by sample 170 and sampling device 175 in FIG. 1. For example, a sampling device may include a surface area that adheres or attaches to a sample material. See, for example, U.S. Pat. No. 6,102,892 to Putzer et al., titled "Diaper with pleats for containment of liquid and solid wastes," and U.S. Pat. No. 6,423,884 to Oehmen, titled "Absorbent article having apertures for fecal material," which are incorporated by reference herein.

Systems and methods described herein include one or more analysis device. As shown in FIG. 1, an analysis device 177, 187 may come in direct contact with or be integrated with the sampling device 175, 185 for analysis of a sample. For example, a sampling device including a swab or absorbent material may be placed directly into an analysis device. In some embodiments, a portion or component of a sample may be extracted prior to analysis. For example, excess fluid may be removed from a sample prior to analysis. For example, a portion of a sample may be concentrated in a gradient or by centrifugation prior to analysis. For example, proteins or nucleic acids may be purified from a sample prior to analysis.

An analysis device may analyze a sample by any number of techniques, depending on the type of sample and parameters of the assays utilized. For example, the analysis device may include culturing microbes from the sample and then testing them for one or more characteristics such as growth rate, visual appearance, antibiotic resistance, antibiotic susceptibility, culturing parameters including but not limited to growth on specific nutrient sources, or culture staining. For example, one or more samples may be cultured in an analysis device that also allows for testing in vitro response to antimicrobial agents, such as described in U.S. Pat. No. 7,384,778 to Chen et al., titled "Methods and devices for the detection of pathogenic microorganisms and their antimicrobial susceptibility," which is incorporated herein by reference. For example, one or more samples may be cultured in a microplate analysis such as the MicroLog™ system available from BIOLOG, Inc, (Hayward Calif.), the brochure for which (Part #00A022, Rev A 01/2007) is herein incorporated by reference. In some embodiments, the microbes present in a sample may be difficult or impossible to culture using standard techniques and therefore must be analyzed using techniques that do not require cell culture. See, for example, US Patent Application No. 2007/0264636 to Crosby and Criddle, titled "Capture and random amplification protocol for identification and monitoring of microbial diversity," and Scanlan and Marchesi Ibid, which are herein incorporated by reference. For example, a sample may be subjected to Gram staining, or florescent in situ hybridization ("FISH") analysis, or total DNA staining with an agent such as SYBR green. See, for example, Ivanov et al., "Specific microbiota direct the differentiation of IL-17-producing T-helper cells in the mucosa of the small intestine," Cell Host and Microbe, 4:377-349 (2008), and Penders et al., "Factors influencing the composition of the intestinal microbiota in early infancy," Pediatrics 118(2): 511-521 (2006), which are herein incorporated by reference. For example, the analysis device may include nucleic acid analysis of the microbes present in the sample. Depending on the embodiment, nucleic acids may be analyzed directly, or may be purified from the sample prior to examination by the analysis device. In some embodiments, DNA from a sample may be purified and then a profile of the sample generated by denaturing gradient gel electrophoresis, or a specific DNA fragment or set of fragments may be profiled using appropriate molecular biology techniques including, but not limited to, "real-time" PCR analysis or sequencing. See, for example, Iapichino et al., "Impact of antibiotics on the gut microbiota of critically ill patients," Journal of Medical Microbiology 57: 1007-1014, (2008), Scalan and Marchesi kid, and Penders et al, Ibid, which are herein incorporated by reference. In some embodiments, a normalized global estimation of the major contributing microbial species may be based on real-time PCR assays, such as described in Ott et al., "Quantification of intestinal bacterial populations by real-time PCR with a universal primer set and minor groove binder probes: a global approach to the enteric flora," Journal of Clinical Microbiology, 42(6):2566-2572 (2004), which is herein incorporated by reference. In some embodiments, breath may be analyzed, such as described in U.S. Pat. No. 7,255,677 to Burch et al., titled "Detection, diagnosis and monitoring of a medical condition or disease with artificial olfactometry," which is herein incorporated by reference.

In some embodiments, a carrier or challenge compound may be administered to an individual prior to sample collection and analysis to improve assay sensitivity. For example, an individual may be given a controlled dosage of a sugar-containing compound prior to sampling of breath as part of a test for small intestine bacterial overgrowth. See, for example, US Patent Applications Nos. 2008/0014184 and 2008/0014185 to Lin and Pimentel, titled "Methods of treating fibormyalgia caused by small intestinal bacterial overgrowth," and "Methods of treating diarrhea and bloating caused by small intestinal bacterial overgrowth" respectively, which are herein incorporated by reference. For example, an individual may be administered carbon isotopes as part of a test for *H. Pylori* infection, see Pathak et al., "Urea breath test for *Helicobacter pylori* detection: present status," Tropical Gastroenterology 25:156-161 (2004), which is incorporated by reference herein.

In some embodiments, a sampling device 104, 115, 125, 135, 145, 155, 165 may include one or more additional device which may yield additional information about the sample collection. For example, the sampling device may include a stopwatch or timekeeping device and record the time when one or more samples are taken, the date of sample collection, or the time interval between samples being collected. The sampling device may also include a temperature monitor or pH monitor and record the temperature or pH at the time a sample is taken.

In some embodiments, a sampling device 104, 115, 125, 135, 145, 155, 165 may communicate with an analysis device 105 remotely, including through wireless transmissions 107. See U.S. patent application to Boyden et al., titled "Adaptive dispensation in a digestive tract, filed on Oct. 23, 2007 and US Patent Application No. 2009/0112191 to Boyden et al. titled "Medical or veterinary digestive tract utilization systems and methods" which are herein incorporated by reference. Such wireless transmissions may assist a user in locating a sampling device located within an individual body at a given time point. An analysis device may also receive crude or incomplete data from one or more sampling device and act to analyze the crude data into a full analysis as described herein. For example, a sampling device may signal remotely, from within a gastrointestinal tract system, information such as the time, date, pH or temperature, and such information may be integrated with data from the analysis of a sample during information processing.

Information from one or more analysis devices may be communicated to at least one computational device for integration into a profile at one or more time points. One or more analysis device may be operably attached to at least one computational device. For example, an analysis device may be operably attached to a computational device through a wire or network connection. In some embodiments, the analysis device and the computational device may be integrated into a single unit. For example, an analysis device may operate such that data from the analysis device automatically outputs to a computational device. Although a laptop computer is shown as computational device 190 in FIG. 1, it is envisioned that in some embodiments there may be a group of computational devices, such as a network or large computer system. A computational device may include digital memory and a user input device such as a mouse, touchpad, touch screen or auditory signal converter. A computational device 190 is operably attached to at least one user interface device 195, such as a monitor, auditory signal generator, light emitter, or electronic ink device.

Although user 197 is shown/described herein as a single illustrated figure, those skilled in the art will appreciate that user 197 may be representative of a human user, a robotic user (e.g., computational entity), and/or substantially any combination thereof (e.g., a user may be assisted by one or more robotic agents) unless context dictates otherwise. In some embodiments, user 197 may be part of a larger medical system, such as a medical team, clinic, hospital, HMO, or office as individual people or as computer-based systems or networks. In some embodiments, a user 197 may be an individual whose gastrointestinal microbes are being evaluated, or a relative, associate or caregiver of such an individual. In some contexts, the user 197 may be a patient. In general, the same may be said of "sender" and/or other entity-oriented terms as such terms are used herein unless context dictates otherwise. As used herein, the user may include, for example, a doctor, nurse, medical personnel, researcher, caregiver, patient or individual, using the system either singly or collectively.

Figure 2:
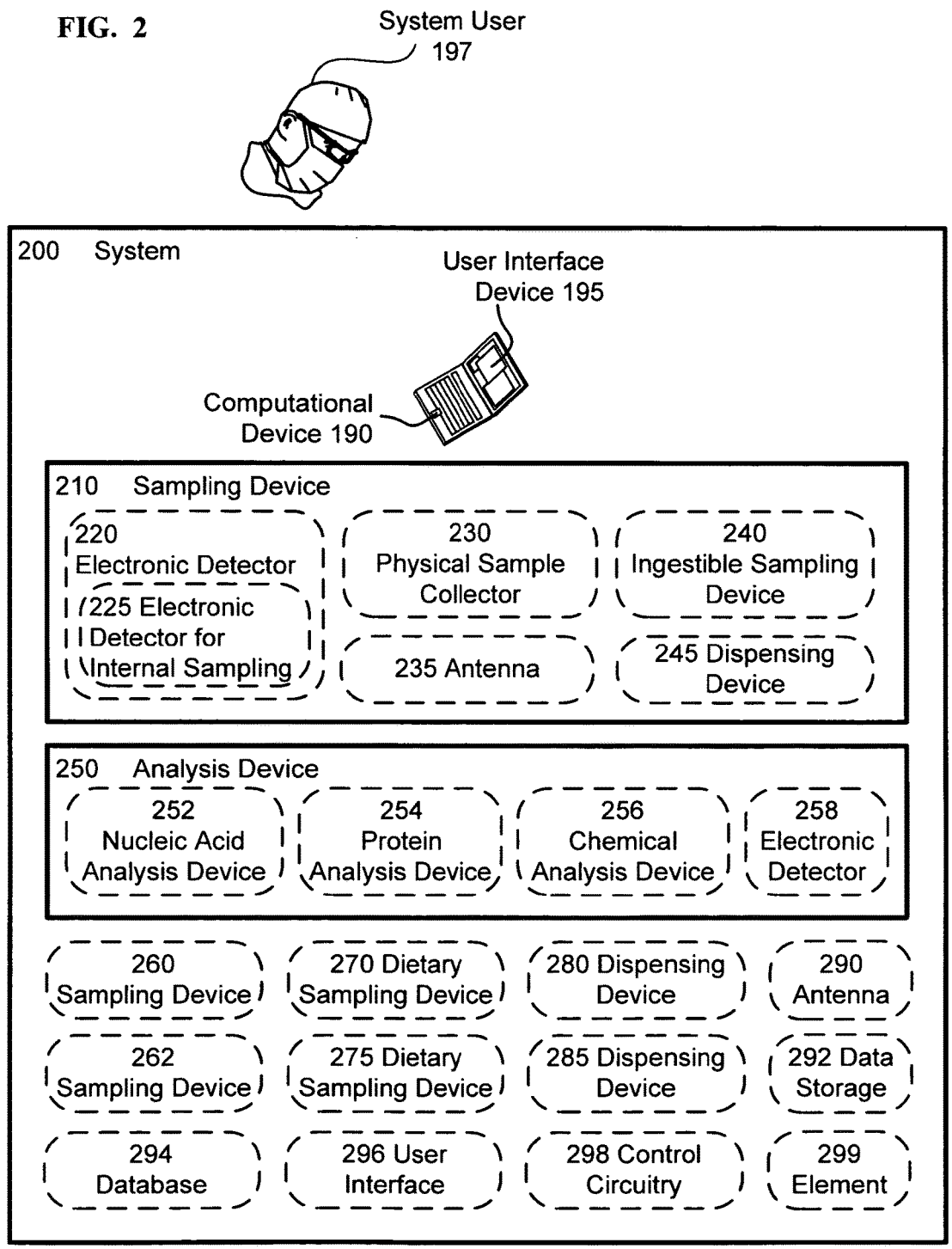
FIG. 2 is a schematic of a system including multiple devices.

FIG. 2 shows aspects of systems such as those described herein. A system 200 for continual modification of intestinal microbes includes at least one sampling device 210 operable for taking at least one sample of an individual's gastrointestinal microbes and at least one analysis device 250 operable for analysis of at least one sample. The system 200 also includes at least one computational device 190, operable for accepting data regarding the analysis of the at least one sample and comparing the data to a standard profile, and at least one user interface device 195 operably connected to the at least one computational device. In some embodiments, the at least one computational device and the at least one user interface device are an integrated unit. A system user 197 may, for example, interface with the system, input data into the system, recognize an indication from the system, or receive output from the system through a user interface (UI) device that may include one or more monitor, keyboard, mouse, voice recognition system or auditory signal generator. In some embodiments, the system 200 may include a sampling device 210 including one or more electronic detector 220. The electronic detector 220 may include an electronic detector 225 operable for sampling internal to a body. See US Patent Application No. 2009/0192449 to Boyden et al., titled "Adaptive dispensation in a digestive tract," filed on Oct. 23, 2007 and US Patent Application No. 2009/0112191 to Boyden et al. titled "Medical or veterinary digestive tract utilization systems and methods" which are herein incorporated by reference. The sampling device 210 may include one or more physical sample collector 230. The sampling device 210 may include at least one antenna 235, such as an antenna operable for sending or receiving data from other parts of the system or external to the system. For example, a sampling device may transmit information relating to sample collection such as time, pH, temperature or sample identification information. For example, a sampling device may receive a signal to take a sample at a specific location within the gastrointestinal system or at a specific time point. One or more sampling device 210 may include at least one ingestible sampling device 240. One or more sampling device 210 may include one or more dispensing devices 245. The analysis device 250 may include one or more nucleic acid analysis device 252. For example, one or more nucleic acid analysis device may include one or more DNA sequencer, PCR machine, "real-time" (RT) PCR machine, mass spectrophotometer, gradient gel device (including denaturing gradient gels) or microscope for examination of stained nucleic acids in a sample. For example, one or more nucleic acid analysis device may include an analysis device that analyses at the metagenomic level, including at the level of analyzing composite characteristics of a group of microbes. The analysis device 250 may include one or more protein analysis device 254. For example, a protein analysis device may include a protein sequencer, a mass spectrophotometer, one or more antibodies forming recognition elements, or a gradient gel device. For example, a protein analysis device may include detecting specific proteins, such as described in U.S. Pat. No. 7,214,479 to Welch et al., titled "*E. coli* O157:H7 C1-INH-binding protein and methods of use," which is incorporated herein by reference. The analysis device 250 may include one or more chemical analysis device 256. A chemical analysis device may detect volatiles, organic compounds, secondary metabolites or enzymes indicative of a microbial population. For example, a chemical analysis device may include a chemical component detector, such as a mass spectrophotometer. The analysis device 250 may include one or more electronic detector 258. For example, an electronic detector may include an "electronic nose" or "electronic tongue" device. See, for example, U.S. Pat. No. 7,255,677 to Burch et al., titled "Detection, diagnosis and monitoring of a medical condition or disease with artificial olfactometry," and U.S. Pat. Nos. 5,571,401 and 5,698,089 to Lewis and Freund, titled "Sensor arrays for detecting analytes in fluids," and US Patent Application 2008/0293997 to Buhlmann and Boswell, titled "Chemical sensor," which are herein incorporated by reference.

In some embodiments, the system receives input from a system user such as a patient, individual, or caregiver and incorporates that information into the analysis parameters or stored information. Input from a system user may be incorporated with data from one or more analysis device, and may form metadata. A system user may input information relating to a specific event, such as an individual going on antibiotic medication, or changing diet, and incorporate that information along with the data generated from an analysis device during that time period to generate relevant metadata. For example, where an individual is undergoing a specific course of antibiotic treatment, that individual or another person may enter the dates and details about the antibiotic treatment into the system, and the system may incorporate this into metadata for the relevant time period. For example, an individual may eat an unusually fatty or sugary meal before a sample is taken, and an individual may input the relevant details of their recent diet into the system. For example, an individual who is undergoing a series of sampling procedures may change diet (such as become a vegetarian, or go on a low-fat diet) at some point during the series. Information relating to the diet change may be input into the system and incorporated into the stored information as, for example, metadata.

A system such as the one diagrammed in FIG. 2 may also include additional elements as desired for a particular embodiment. For example, a system 200 may include at least one additional sampling device, including multiple sampling devices 210, 260, 262. For example, a system 200 may include one or more dietary sampling devices 270, 275. At least one dietary sampling device may be operably connected to the at least one computational device. A dietary sampling device may sample a portion of foodstuffs intended for ingestion by the individual for analysis, such as to yield data on the composition of the foodstuffs. For example, a dietary sampling device may sample a foodstuff for caloric analysis. For example, a dietary sampling device may sample a foodstuff for composition analysis, such as what components are included in a foodstuff mixture. For example, a dietary sampling device may sample a foodstuff for microbial analysis, such as microbial analysis of a fermented or microbe-containing foodstuff such as yogurt, tofu or cheese products. For example, a dietary sampling device may sample partially digested foodstuffs from any region of the gastrointestinal tract for completeness of digestion, rates of digestion, or dietary byproducts. A system 200 may include one or more dispensing devices 280, 285, which may dispense, for example, one or more microbes, antimicrobial agent, prebiotic, prebiotic, synbiotic, or nutritional supplement. For more information on the terms "probiotic" and "prebiotic," and "synbiotic" see Schrezenmeir and de Vrese, "Probiotics, prebiotics, and synbiotics—approaching a definition," American Journal of Clinical Nutrition 73(suppl.): 361S-364S (2001), which is herein incorporated by reference. Briefly, a "probiotic" may be described as "a preparation of or a product containing viable, defined microorganisms in sufficient numbers, which alter the microflora (by implantation or colonization) in a compartment of the host and that exert beneficial health effects on this host," while "prebiotic" may be described as "a non-digestible food ingredient that beneficially affects the host by selectively stimulating the growth and/or activity of one or a limited number of bacteria," see Schrezenmeir and de Vrese, Ibid. For example, the one or more dispensing devices may dispense one or more specific antimicrobial compounds, such as those described in U.S. Pat. No. 7,211,426 to Bruessow et al., titled "Isolated phages and their use in food or pet food products," and U.S. Pat. No. 7,371,375 to Zimmer et al., titled "Protein," and US Patent Application No. 2008/0146609 to Guiles et al., titled "Substituted Thienopyridone Compounds With Antibacterial Activity," and US Patent Application No. 2008/0170991 to Shi et al., titled "Selectively targeted antimicrobial peptides and the use thereof," and US Patent Application No. 2008/0171376 to Scholl and Williams, titled "Modified bacteriocins and methods for their use," and US Patent Application No. 2008/0220103 to Birnbaum et al., titled "Method for treating/controlling/killing fungi and bacteria on living animals," all of which are herein incorporated by reference. For example, the one or more dispensing devices 280, 285 may dispense a pharmaceutical composition such as those described in U.S. Pat. No. 6,706,287 to Ranganathan et al, titled "Prebiotic and probiotic compositions and methods for their use in gut-based therapies," or as described in US Patent Application No. 2004/0028689 to Borody, titled "Probiotic recolonisation therapy," which are herein incorporated by reference. For example, the one or more dispensing devices may dispense slowly digestible starch and fermentable dietary fiber compounds such as those described in US Patent Application No. 2007/0196437 to Hamaker et al., titled "Slowly digesting starch and fermentable fiber," and in Napolitano et al., "Potential prebiotic activity of oligosaccharides obtained by enzymatic conversion of durum wheat insoluble dietary fibre into soluble dietary fibre," Nutrition, Metabolism & Cardiovascular Diseases, in press, available online as of 20 Sep. 2008, DOI: 10.1016/j.numecd.2008.07.005, which are incorporated herein by reference. For example, the one or more dispensing devices may dispense at least one lactose-reduced dairy composition, such as those described in US Patent Application No. 2007/0196439 to Catani and Robinson, titled "Lactose-reduced dairy compositions and related methods," which is incorporated herein by reference. At least one dispensing device may be operably connected to the at least one computational device. For example, the at least one computational device may receive information from a dispensing device relating to time, quantity and identity of material dispensed. For example, the at least one computational device may signal a dispensing device relating to time, quantity, location or identity of material to dispense. A system 200 may include one or more antenna 290 configured for signaling between parts of the system or with elements outside of the system. A system 200 may include data storage 292, such as digital data storage including recordable type medium formats such as floppy disk, hard disk drive, digital tape, computer memory, etc. A system 200 may include a database 294. For example, a database may include information on previous samples taken from a specific individual, or information regarding the health history or status of an individual or metadata such as comments from the individual or physician. A database may also contain information relating to a set of standard profiles or possible interventions that may be suggested by the system to at least one system user. A system 200 may include at least one user interface 296, for example at least one display, touch screen, auditory response system, keypad, mouse, or other interface device. A system 200 may include control circuitry 298, which may include electronic circuitry having one or more paths of electrical current constructed and arranged to implement various functions as described herein. A system 200 may include one or more elements 299 selected by the system designer.

Figure 3:
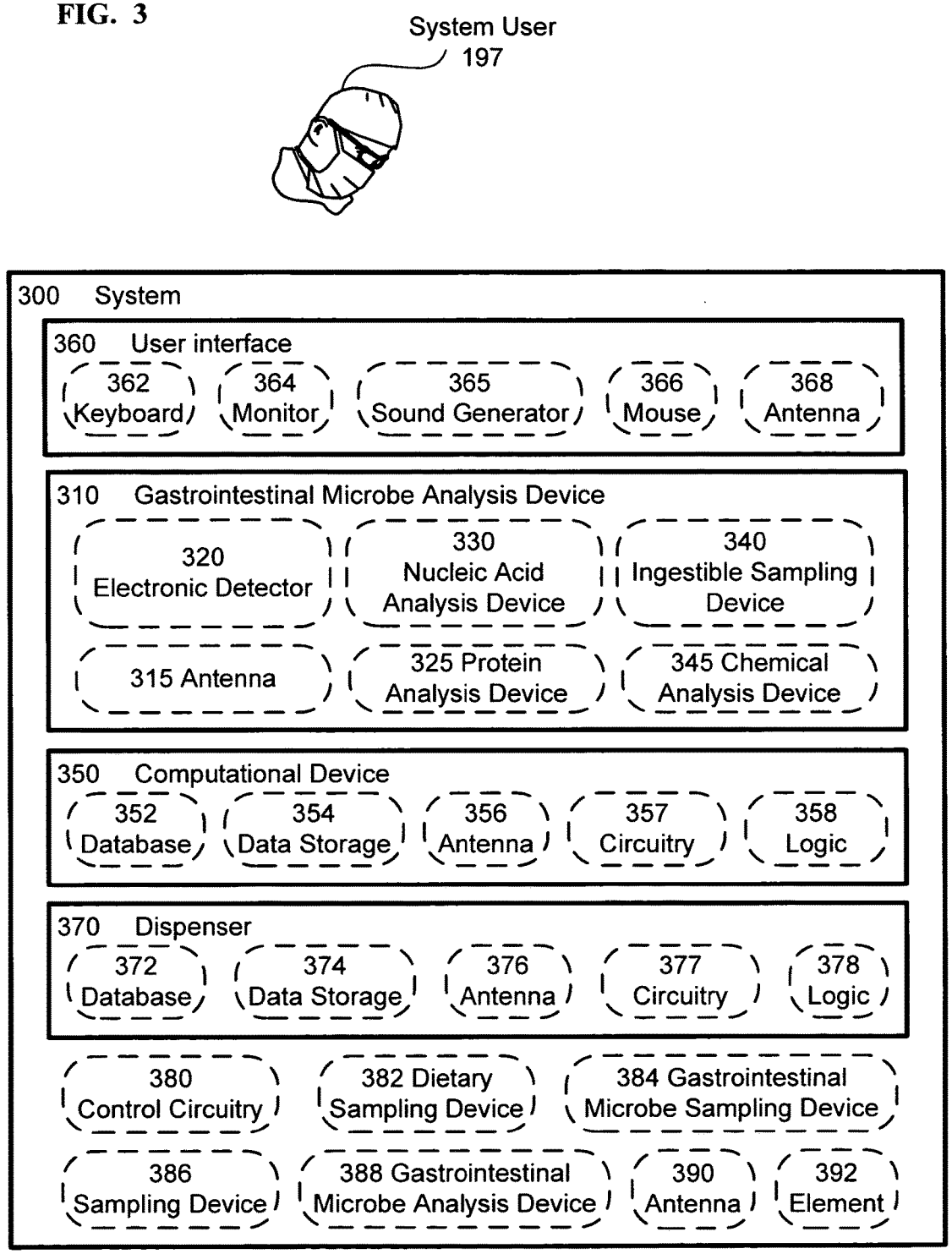
FIG. 3 is a schematic of a system including multiple devices.

FIG. 3 depicts aspects of a system 300. A system for monitoring and introducing gastrointestinal microbes into a mammalian gastrointestinal tract over time includes at least one gastrointestinal microbe analysis device 310, at least one computational device 350, at least one user interface 360 operably connected to the at least one computational device 350, and at least one dispenser 370 operably connected to the at least one computational device 350. In some embodiments, the at least one gastrointestinal microbe analysis device may be reusable, such as an endoscopy device that may be recharged or refurbished before reuse. In some embodiments, the at least one gastrointestinal microbe analysis device may be modular, such as a device that may have one or more modules removed and replaced or swapped for another module. In some embodiments, the at least one gastrointestinal microbe analysis device 310 may include one or more nucleic acid analysis device 330. In some embodiments, the at least one gastrointestinal microbe analysis device 310 may include one or more protein analysis device 325. In some embodiments, the at least one gastrointestinal microbe analysis device 310 may include one or more chemical analysis device 345. In some embodiments, the at least one gastrointestinal microbe analysis device 310 may include one or more electronic detector 320. In some embodiments, the at least one computational device 350 is operably connected to the at least one gastrointestinal microbe analysis device 310. For example, the at least one computational device may be operably connected to the at least one gastrointestinal microbe analysis device through a wired or wireless connection, or a network. In some embodiments, the at least one computational device may be integrated with the at least one gastrointestinal microbe analysis device, such as an analysis device that is integrated with a computer system as part of its standard operation. In some embodiments, the at least one gastrointestinal microbe analysis device 310 includes at least one antenna 315, such as an antenna operable for sending or receiving communications from other parts of the system or external to the system. An antenna may be configured to send or receive communications from various parts of the system or from one or more devices external to the system. In some embodiments, a gastrointestinal microbe analysis device 310 may be an ingestible sampling device 340.

Depending on the embodiment, the at least one dispenser 370 may be configured to dispense one or more materials. For example, at least one dispenser may be configured to dispense at least one microbe, antibiotic, antifungal, prebiotic agent, probiotic agent, or nutritional supplement. For more information regarding probiotics, see Blandino et al., "Probiotics: overview of microbiological and immunological characteristics," Expert Rev Infect Ther 6(4):497-508 (2008), which is herein incorporated by reference. The at least one dispenser 370 may include a database 372, for example a database of potential agents possible to dispense, or of codes to signal or indicate when a specific dispensation protocol should be initiated. The at least one dispenser 370 may include at least one data storage unit 374, for example a look-up table including sequences of events involved in certain dispensation protocols. In some embodiments, the at least one dispenser 370 may include at least one antenna 376. For example, the antenna may be configured to send a signal when the dispensation begins or ends, or may be configured to receive a signal initiating a dispensation protocol. In some embodiments, the at least one dispenser 370 may include circuitry 377, for example control circuitry for the dispenser. In some embodiments, the at least one dispenser 370 may include logic 378, such as dispensing protocols implemented as hardware, software or firmware.

Depending on the embodiment, the at least one computational device 350 may include at least one database 352, for example containing information regarding an individual or group of individuals, one or more individual or standard profiles, or operating parameters of the system. In some embodiments, the at least one computational device 350 may include at least one data storage unit 354, for example data storage in a hard disk drive, a digital tape, or a computer memory. The data storage may be operable for storing data input during operation of the system, for example information from the analysis device or the user interface. The data storage may be operable for storing data preexisting to the system operation, for example one or more standard profiles or individual identifiers. In some embodiments, the at least one computational device 350 may include at least one antenna 356, for example at least one antenna operable for transmitting information relating to the analysis device or the dispensing device. The at least one antenna may also receive input from an outside source, such as an external network or database. In some embodiments, the at least one computational device 350 may include circuitry 357. For example, the circuitry may include control circuitry for the system as a unit. In some embodiments, the at least one computational device 350 may include logic 358, for example integration protocols to integrate information relating to the individual and information from the sample analysis into a profile for a time point. The at least one computational device 350 may include logic 358 which includes protocols for the comparison of an individual profile to a standard profile.

In some embodiments, the at least one user interface 360 may include any type of user interface (UI) configured to be operable for a particular embodiment. For example, the at least one user interface 360 may include at least one keyboard 362, at least one monitor 364 (which may be a touch-sensitive monitor or an E-ink device), at least one sound generator 365 (such as a sound signal generator for beeps, hums, alarms or the like, or a sound generator operable for production of artificial human speech), and at least one mouse 366. The at least one user interface 360 may also include at least one antenna 368, for example an antenna operable for receiving transmitted signals that may be translated into an indicator for at least one system user.

In addition, a system 300 may include at least one additional gastrointestinal microbe analysis device 388. For example, a system 300 may be operable to include input from two or more distinct types of gastrointestinal microbe analysis devices. For example, a system 300 may be operable to include input from two or more gastrointestinal microbe analysis devices of the same type analyzing samples at distinct times. A gastrointestinal microbe sampling device may be ingestible. A system 300 may include at least one dietary sampling device 382. The at least one dietary sampling device 382 may be operably connected to the at least one computational device 350, for example for the transmission of information between the at least one computational device 350 and the at least one dietary sampling device 382. A system 300 may include at least one gastrointestinal microbe sampling device 384. A system 300 may include control circuitry 380, for example circuitry for integrating the operation of the components of the system. A system 300 may include a sampling device 386, for example a sampling device for sampling extra-gastrointestinal samples from an individual such as blood or urine samples. A system 300 may include at least one antenna 390, such as for transmitting information to or receiving information from outside of the system. A system 300 may include at least one additional element 392.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either subcomponent operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

FIG. 4 illustrates some aspects of the systems and methods as described herein. A computer-implemented method 400 may include: accepting data describing an individual's gastrointestinal microbes present at a first time 410; accepting data regarding the individual's status at the first time 420; integrating, on a computing device, the accepted data regarding an individual's gastrointestinal microbes and the accepted data regarding the individual's health status into an individual profile for the first time 430; comparing the individual profile for the first time to a standard profile 440; and indicating, to at least one system user, one or more interventions relating to gastrointestinal microbes associated with directing the individual profile for the first time to be closer to the standard profile 450. The method steps may be repeated multiple times at time intervals appropriate to the particular embodiment, for example daily while an individual is undergoing a course of antibiotic therapy, or weekly while an individual is undergoing chemotherapy. The method steps may be repeated daily, weekly, monthly or in other periodic intervals. The method steps may be repeated at intervals selected to be convenient for the individual, such as during regular medical exams or routine screening events. The computer-implemented method may be implemented on a system with a user interface (UI) to at least one system user 460. A system user may include, for example, the individual, a healthcare worker, a physician, nurse, occupational therapist, counselor, dietician, family member or caregiver. A system user may include a group of individuals or a computational or robotic entity such as a network or a health-related system. An individual's health status may include, for example, information relating to the individual's medical history, metabolic status, indicators of health or disease, body mass index (BMI), family medical history, genomic data, mitochondrial genomic data, or epigenomic data. Accepted data regarding an individual's gastrointestinal microbes may include, for example, estimated numbers of various types of gastrointestinal microbes in one or more particular regions of the gastrointestinal system, or estimated relative levels of different species, classes or groups of microbes. Accepted data regarding an individual's gastrointestinal microbes may include minimum or maximum values or ranges of data. Accepted data regarding an individual's gastrointestinal microbes may include extrapolations based on indirect microbial analysis, such as analysis of metabolites of microbial populations or dietary products or digestion products from the gastrointestinal tract. Accepted data regarding an individual's gastrointestinal microbes may include extrapolations based on an individual's diet, such as their dietary intake of microbe-containing foodstuffs, such as probiotics, yogurts, cheeses, or fermented foods. Accepted data regarding an individual's gastrointestinal microbes may include extrapolations based on an individual's recent medical treatments, such as drug therapies or surgical events. Accepted data regarding an individual's gastrointestinal microbes may include extrapolations based on an individual's environmental exposure from an outside source, such as family members, other individuals in an institution or care facility, or other members of the regional population. Accepted data may include "metadata" such as comments explaining anomalies.

A standard profile, as used herein, refers to an extrapolated gastrointestinal microbial profile from a hypothetical standard healthy individual, such as a hypothetical individual with similar personal history as the sampled individual. A standard profile may include a range or scale of values for various parameters of the profile. For example, a standard profile may be an idealized profile based on information from a group of individuals. A standard profile may be extrapolated based on information from a group of individuals of the same or similar ethnic group, age, medical history, gender, national origin, or genomic status. For example, a standard profile may be extrapolated from healthy infants born at full term with a similar ethnic background or born in a single hospital. For example, a standard profile may be extrapolated from healthy infants born at full term who are exclusively breastfed. For example, a standard profile may be extrapolated from information regarding the individual gastrointestinal microbial profiles of a group of healthy individuals of one gender in a certain age range of a particular ethnic group. For example, a standard profile may be extrapolated from information regarding the individual gastrointestinal microbial profiles of a group of healthy men aged 50-60 who are all African-American. For example, a standard profile may be extrapolated from information regarding the individual gastrointestinal microbial profiles of a group of healthy women aged 35-40 who are all of Chinese descent. For example, a standard profile may be extrapolated from information regarding the individual gastrointestinal microbial profiles of a group of healthy men aged 60-70 who were all born in India but immigrated to North America as young adults. For example, a standard profile may be extrapolated from information regarding the individual gastrointestinal microbial profiles of a group of individuals in an extended family, such as siblings, children, grandchildren, parents, aunts, uncles, cousins and grandparents. For example, a standard profile may be extrapolated from information regarding the individual gastrointestinal microbial profiles of a group of individuals who share one or more genetic or genomic traits, such as DNA sequences, single-nucleotide polymorphic (SNP) alleles, restriction fragment polymorphism alleles (RFLP) alleles, karyotype characteristics, or cDNA assay results. An individual's genetic information may include, for example, information from one or more medical tests that incorporates one or more genetic assay, one or more nucleic acid array, or one or more specific locus assay. In some embodiments, a standard profile may be based on earlier assay data from the same individual, such as when the individual was in a healthy or pre-medical intervention state, while in others it may be based on assay data from other individuals as a composite or theoretical ideal.

It is envisioned that the one or more interventions relating to gastrointestinal microbes associated with directing the individual profile for the first time to approximate or be closer to the standard profile may be determined by calculating, on a computing device, the relative differences between the individual profile for the first time and the standard profile, then indicating which differences may be amenable to specific interventions. For example, where the individual profile includes a reduction in total diversity of microbial population, an intervention may include the dispensation of a group of microbes, each of which is reduced in the individual profile relative to the standard profile. Such a situation may exist, for example, in an individual who has recently undergone a medical procedure including the administration of antibiotics, antifungals, or suppression of the gastrointestinal system, such as surgery, chemotherapy, or anesthesia. For example, where an individual profile includes a reduction in a group or class of gastrointestinal microbes relative to the standard profile, a suggested intervention may include the reintroduction of one or more group or class of gastrointestinal microbes that is reduced in the individual profile, or the addition of one or more probiotic (or prebiotic or synbiotic) associated with increased growth of the desired group or class of microbes. For example, where the individual profile includes an increase in total diversity of microbial population, an intervention may include the dispensation of at least one antimicrobial agent associated with decreasing the diversity to be closer to the diversity seen in the standard profile. For example, where an individual profile includes an increase in a group or class of gastrointestinal microbes relative to the standard profile, a suggested intervention may include the introduction of one or more antimicrobial agents that are associated with the reduction in numbers of the elevated group or class. For example, an intervention may include one or more specific antibiotic, antifungal or chemical agents predicted to selectively reduce the population of a group or subset of microbes. In some embodiments, a combination of the selective increase and the selective decrease of microbial groups or classes may be indicated. In some embodiments, one or more intervention may include additional suggested components associated with an increase in the health of the individual. One or more indicated intervention may include interventions such as the inclusion or reduction of prebiotics, probiotics, synbiotics, or nutritional therapies to an individual's diet. One or more indicated intervention may include one or more antibiotics, antimicrobials or antifungal agents. One or more indicated intervention may include one or more suggestion of additional hydration measures, such as increasing water drunk by the individual. One or more indicated intervention may include avoidance of some foodstuffs, such as those containing dairy products, wheat gluten, processed or cured meats, salts, some spices, or those with excessive fat content. One or more indicated intervention may include avoidance of some beverages, such as alcoholic beverages, caffeinated beverages, beverages with a high sugar content, or beverages containing fermented products like tofu or yogurt.

FIG. 5 depicts variations of the methods illustrated in FIG. 4. In some embodiments, accepting data regarding the individual's health status at the first time 420 may include accepting data regarding the individual's diet 500. For example, accepting data regarding the individual's diet 500 may include accepting data as to the individual's recent diet, planned diet or standard diet. For example, accepting data regarding the individual's diet 500 may include accepting data indicating that the individual is a vegetarian, or does not eat dairy products, or generally eats salads for lunch. In some embodiments, accepting data regarding the individual's health status at the first time 420 may include accepting data regarding at least one metabolic state of the individual 510. For example, accepting data regarding at least one metabolic state of the individual may include accepting data regarding a disease state such as autoimmune disease, infectious disease, or cancer incidence. For example, accepting data regarding at least one metabolic state of the individual may include accepting data regarding a non-ideal state, such as metabolic syndrome, hypertension, poor circulation, immune suppression, or recent history of serial or chronic infectious disease.

In reference to FIG. 5, in some embodiments integrating, on a computing device, the accepted data regarding an individual's gastrointestinal microbes and the accepted data regarding the individual's health status into an individual profile for the first time 430 may include integrating the accepted data into an individual profile which includes a range of values for the data 520. For example, if an individual has had multiple gastrointestinal samples taken and analyzed at the same or different time points, the subsequent data may yield a range of values that are integrated into an individual profile as a standard range of values for that individual.

FIG. 6 illustrates variations of the method depicted in FIG. 4. For example, some embodiments may include signaling for release of one or more gastrointestinal microbe 600. For example, where the method is implemented on a system including a dispensing device, the dispensing device may be sent a signal triggering the release of one or more species or class of gastrointestinal microbe. For example, some embodiments may include signaling for release of one or more probiotic agent 610. For example, some embodiments may include associating the individual profile with one or more interventions relating to gastrointestinal microbes to direct the individual profile for the first time to be closer to the standard profile 620.

FIG. 7 depicts optional embodiments of the method shown in FIG. 4. Some embodiments may include accepting data describing an individual's gastrointestinal microbes present at a second time, accepting data regarding the individual's health status at the second time, integrating, on a computing device, the accepted data regarding an individual's gastrointestinal microbes and the accepted data regarding the individual's health status into an individual profile for the second time, comparing the individual profile for the second time to the standard profile, and indicating one or more alterations in gastrointestinal microbes associated with directing the individual profile for the second time to be closer to the standard profile 700. For example, an individual may be sampled a second or subsequent time and the individual profile for the second time may be distinct from the individual profile at the first time, and so any intervention may be revised relative to the new information. Some embodiments may include accepting at least one personal parameter relating to the individual, and selecting the standard profile to correspond with one or more of the at least one personal parameter 710. Personal parameters may include, for example, age, gender, ethnicity, nationality, birthplace, genetic status, genomic status, disease state or metabolic state. For example in some embodiments, a standard profile may be selected based on a shared personal parameter between the standard profile and the individual. For example, the standard profile may be a composite profile based on information derived from gastrointestinal samples taken from healthy, full-term breast-fed infants and the sampled individual may also be an infant. For more information regarding factors influencing the establishment of gastrointestinal microbes in infants, see Adlerberth, "Factors influencing the establishment of the intestinal microbiota in infancy," Nestle Nutr Workshop Ser Pediatr Program, 62:13-33 (2008), and Penders et al., "Factors influencing the composition of the intestinal microbiota in early infancy," Pediatrics 118(2):511-521 (2006), which are herein incorporated by reference. For example, the standard profile may be derived from information relating to gastrointestinal samples taken from a group of healthy men aged 70-80 and the individual may be a 75 year old man. For example, the standard profile may be based on information from gastrointestinal samples taken from Caucasian women in their 20s, and the individual may be a Caucasian woman in her 50s. For example, the standard profile may be based on data obtained from gastrointestinal samples taken from healthy immigrants from India who have lived in North America at least 10 years and the individual may have recently emigrated from India, such as perhaps within the past six months. For example, the standard profile may be derived from information relating to gastrointestinal samples taken from persons who have otherwise tested positive for a particular allele or set of alleles, such as specific alleles of surface receptor proteins, and the sampled individual may also have tested positive for the same allele or a subset of relevant alleles. For example, the standard profile may be derived from information relating to gastrointestinal samples taken from persons who independently have a distinct set of attributes in a specific assay, such as a DNA-based genetic assay or a set of antibody tests, and the sampled individual may also have the same distinct set of attributes when tested by the same assay.

FIG. 8 illustrates aspects of the method depicted in FIG. 4. The method may include, in some embodiments, creating, on a computing device, at least one difference listing between the individual profile for the first time and the standard profile, associating at least one intervention with minimizing the at least one difference listing, and indicating, to at least one system user, at least one intervention associated with minimizing the at least one difference listing 800. For example, if the difference listing indicates an overgrowth of a class or group of microbes in the individual profile relative to the standard or reference profile, an intervention may include suggesting one or more antimicrobial agent that is known to affect the excess class or group of microbes relative to other microbes, or an intervention may include suggesting a prebiotic which encourages growth of other classes or groups of microbes relative to the excess group and therefore adjust their relative levels. For example, if a difference listing indicates a relative lack of a class of group of microbes relative to the standard or reference profile, an intervention may include suggesting one or more prebiotic that is expected to encourage growth of the reduced group, or a probiotic containing the lacked microbes or a synbiotic with the appropriate combination of the two. It is envisioned that an intervention may also include aspects that support the primary components, such as suggestions to avoid foods that may contain microbes that appear to be in overabundance relative to the standard profile, or foods that would otherwise interfere with the suggested intervention such as excessively spicy foods, highly sugary foods or beverages, alcoholic beverages, highly processed foods, or foods containing high levels of preservatives. As shown in FIG. 8, the method may include, in some embodiments, accepting data describing an individual's gastrointestinal microbes present at a second time, accepting data regarding the individual's health status at the second time, integrating, on a computing device, the accepted data regarding an individual's gastrointestinal microbes and the accepted data regarding the individual's health status into an individual profile for the second time, comparing the individual profile for the second time to the individual profile for the first time, and indicating to at least one system user at least one difference between the individual profile for the second time and the individual profile for the first time 810. For example, a system carrying out the method may indicate to a system user how the relative levels of at least one group or class of microbes may have changed between a first sampling and a second or subsequent sampling. In some embodiments, the first time of sampling may be a reference time point, with an associated reference sample to set a baseline profile and therefore monitor individual profile progressions from the initial time forward. In some embodiments, an individual profile for a second or subsequent time may be used to evaluate the effectiveness of any intervention. For example, if a specific prebiotic agent was suggested as part of the initial intervention strategy and the second or subsequent profile does not indicate a relative change in microbe levels, a different prebiotic agent may be suggested. For example, if a specific antibiotic agent was suggested as part of the initial intervention strategy and the second or subsequent profile does not indicate a relative change in microbe levels, a different antibiotic agent may be suggested. For example, if a specific antibiotic agent was suggested as part of the initial intervention strategy and the intervention had to be discontinued due to allergic reaction or other ill affects, a different intervention strategy may be suggested after a subsequent profile. In some embodiments, the method includes comparing the individual profile for the second time to the standard profile, and indicating to at least one system user at least one difference between the individual profile for the second time and the standard profile 820. For example, a relative increase or decrease in a specific group or class of microbes may be indicated. Such information may be of use, for example, in evaluating the effectiveness of any intervention strategy or agent.

FIG. 9 depicts a computer-implemented method 900 for suggesting adjustments to gastrointestinal microbe profiles over time. The method includes accepting data describing an individual's gastrointestinal microbes present at an initial time 910. For example, the data may relate to a sample taken at a first or initial time. The method includes comparing, on a computing device, the data relating to an individual's gastrointestinal tract microbial composition at an initial time with at least one standard gastrointestinal tract microbial composition 920. For example, the computing device may use graphing methods, tabular formats, or statistical methods to compare the data sets. In some instances, the data may include ranges or sets of values. The method includes identifying differences between the data relating to the individual's gastrointestinal tract microbial composition at an initial time and one or more of the at least one standard gastrointestinal tract microbial composition 930. For example, absolute differences or relative differences may be identified. In some instances, a lack of differences or unity between the data sets may also be identified. The method includes creating an initial difference listing of the identified differences between the data relating to the individual's gastrointestinal tract microbial composition at an initial time and one or more of the at least one standard gastrointestinal tract microbial composition 940. The initial difference listing may be communicated to a system user. The method includes creating at least one initial action plan to alter the individual's gastrointestinal tract microbial composition to minimize the difference listing 950. For example, the action plan may include one or more intervention strategies. An action plan may include suggesting the ingestion of prebiotic agents, probiotic agents, or antimicrobial agents by the individual. An action plan may include suggesting the avoidance of certain foods or beverages, or increasing intake of some foods and beverages. An action plan may include suggesting that the individual drink sufficient fluids, exercise regularly, or include nutritional supplements. In some instances, the action plan may include the removal and replacement of gastrointestinal flora such as described in U.S. Pat. No. 6,645,530 to Borody, titled "Treatment of gastro-intestinal disorders," which is herein incorporated by reference. The method includes indicating one or more of the at least one initial action plan to at least one system user 960. For example, if the system user 970 is a healthcare professional, he or she may integrate the action plan into any medical care plans for the individual. For example, if the system user 970 is a dietician or therapist, he or she may explain at least one action plan to the individual and make specific suggestions regarding diet and therapy that includes the action plan. In some instances, more than one action plan may be indicated and the system user may evaluate the indicated plans based on other criteria, such as ease of implementation, personal preference of the individual, cost, or other individual factors.

FIG. 10 illustrates embodiments of the method shown in FIG. 9. In some embodiments, creating at least one initial action plan to alter the individual's gastrointestinal tract microbial composition to minimize the difference listing 950 may include wherein the at least one initial action plan includes one or more dietary suggestions 1000. For example, an action plan may include suggesting the avoidance of certain foods or beverages, or increasing intake of some foods and beverages. In some embodiments, the method may include accepting data relating to an individual's gastrointestinal tract microbial composition at a second time, comparing, on a computing device, the data relating to an individual's gastrointestinal tract microbial composition at a second time with the initial difference listing, creating a second difference listing, creating at least one second action plan to alter the individual's gastrointestinal tract microbial composition, and suggesting one or more of the at least one second action plan to the system user 1010. For example, the method may be implemented over time and an individual may provide serial samples over time, with the goal of evaluating the gastrointestinal microbial profile of the individual on a recurring basis, or for the evaluation of the effectiveness of an intervention.

FIG. 11 shows embodiments of the method diagrammed in FIG. 9. A method may include accepting data relating to the individual's personal history, and selecting one or more of the at least one standard gastrointestinal tract microbial composition in relation to the individual's personal history 1100. For example, if a specific standard gastrointestinal tract microbial composition originates from data obtained from persons with a particular personal history and the individual shares that personal history, the specific standard gastrointestinal tract microbial composition may be selected for comparison. For example, personal history may include residence type (such as institutional or private home), country of origin, medical history, diagnosis, usual dietary habits (such as vegetarianism or habitual red meat eating), or usual exercise habits. A method may include accepting data regarding at least one personal parameter of the individual, creating an action plan in relation to the accepted data regarding the at least one personal parameter of the individual, and indicating the action plan in relation to the accepted data regarding the at least one personal parameter of the individual to a system user 1110. For example, a personal parameter of an individual may include a factor or preference of the individual that may influence the effectiveness of an action plan. A personal parameter may include, for example, age, dietary restrictions based on medical, social or religious indications, known allergies or sensitivities, weight or size of the individual, availability of components of the action plan to the individual, cost, or other medical therapies which the individual is currently taking or may be taking in the future. Some potential components of an action plan will not be suitable for some individuals based on one or more personal parameters of the individual. For example, a diabetic may have dietary restrictions that any action plan for a diabetic individual would ideally take into account. For example, some components of an action plan may not be available to an individual, such as an individual with limited mobility who is unable to obtain or consume some foodstuffs. For example, an individual may have surgery scheduled in the foreseeable future, and any action plan would have to be able to be implemented in conjunction with any restrictions relative to the surgery. For example, individuals being treated with the anticoagulant Warfarin (i.e. Coumadin or Waran) should maintain a steady rate of vitamin K intake and any action plan for individuals prescribed Warfarin should incorporate the estimated vitamin K levels of any suggested dietary changes. A system user such as a healthcare professional or caregiver may enter data regarding at least one personal parameter of the individual into a computer system implementing this method and the system may rank, prioritize or highlight a group of potential action plans for indication to the system user that take into account the personal parameter. For example, an action plan for an obese individual may include in part compositions such as those described in U.S. Pat. No. 6,565,847 to Gorsek, titled "Thermogenic weight management composition," and U.S. Pat. No. 6,641,808 to Bojrab, titled "Composition for treatment of obesity," and US Patent Application No. 2005/0239706 to Backhed et al, titled "Modulation of fiaf and the gastrointestinal microbiota as a means to control energy storage in a subject," which are all herein incorporated by reference. For example, an action plan for an individual concerned about intestinal gas production in relation to the intervention may include a composition such as described in US Patent Application No. 2006/0193845 to Watson et al., titled "Combination therapy for controlled carbohydrate digestion," which is herein incorporated by reference. For example, an action plan for an individual otherwise prescribed antibiotics such as ampicillin or piperacillin may include in part compositions such as those described in Stiefel et al., "Orally administered β-lactamase enzymes represent a novel strategy to prevent colonization by *Clostridium difficile,*" Journal of Antimicrobial Chemotherapy, 62:1105-1108 (2008), which is incorporated herein by reference. For example, if an individual has been diagnosed with inflammatory bowel disease (IBD), the action plan may include administration of compositions such as those described in US Patent Application No. 2007/0104712 to Ashkenazi and Ward, titled "Treatment of Inflammatory Bowel Disease with IFN-Gamma Inhibitors," and US Patent Application No. 2007/0123460 to Chang and Petrof, titled "Probiotic compounds from *Lactobacillus* GG and uses therefore," and US Patent Application No. 2007/0128303 to Chang and Petrof, titled "Anti-inflammatory, cytoprotective factor derivable from a probiotic organism," and US Patent Application No. 2007/0178078 to Khoo, titled "Method for modifying gut flora in animals," which are herein incorporated by reference. For example, an action plan for an infant or child may include formula or milk supplements containing oligosaccharide mixtures such as those described in US Patent Application No. 2009/0092729 to Sprenger et al., titled "Oligosaccharide mixture," which is herein incorporated by reference. For example, if an individual has been diagnosed with a neurodegenerative disease, the action plan may include administration of nutritional compositions such as those described in US Patent Application No. 2008/0145451 to Hageman and Bindels, titled "Composition for relieving discomfort," which is herein incorporated by reference. For example, an action plan for an individual with a history of lactic acidosis may include a composition such as described in U.S. Pat. No. 7,011,826 to Rowe and Al Jassim, titled "Control of acidosis," which is herein incorporated by reference. For example, if an individual has been diagnosed with an autoimmune disease, the action plan may include administration of nutritional compositions such as those described in US Patent Application No. 2008/0146510 to Wong and Lam which is herein incorporated by reference. The method may include signaling at least some portion of the indicated one or more action plans to one or more dispenser 1120. For example, if the method is implemented as part of a healthcare system, a portion of the action plan may include specific medications and the system may signal for dispensation of those medications. For example, if the method is implemented as part of an institutional dietary program, the food providers may be signaled to provide specific foods to the individual. For example, a food provider may be signaled to include nutritional additives in the food preparation, such as those described in US Patent Application No. 2008/0102162 to Delcour et al., titled "Prebiotic preparation," which is herein incorporated by reference. For example, the method may include signaling for dispensation of at least one pharmaceutical composition such as those described in U.S. Pat. No. 6,706,287 to Ranganathan et al, titled "Prebiotic and probiotic compositions and methods for their use in gut-based therapies," which is herein incorporated by reference. For example, if the individual is also taking a course of antibiotics, the method may include signaling for the dispensation of pharmaceutical compounds such as those described in US Patent Application No. 2007/0105791 to Sears et al., titled "Method of treating *clostridium difficile*-associated diarrhea," which is herein incorporated by reference.

Systems and methods as described herein may be used for continual modification of intestinal microbes, for example to monitor and influence the growth of subpopulations of intestinal microbes over time. Other aspects of the systems and methods described herein are described in the examples below.

EXAMPLES

Example 1

To improve infant health by evaluating and modifying intestinal microbial flora, a system is described to: 1) periodically determine the microbial flora present (microbial profile) in an individual infant's intestine; 2) integrate medical data related to the infant such as genotype, epigenotype, mitochondrial genotype, gender, race, gestational age, birth weight, mode of delivery, type of infant feeding, antibiotic use, viral infections, bacterial infections, and family history; 3) determine and select a reference microbial profile that integrates data regarding the abundance and diversity of intestinal microbes with medical information, such as genotype, epigenotype, mitochondrial genotype, gender, race, gestational age, birth weight, mode of delivery, type of infant feeding, antibiotic use, viral infections, bacterial infections, and family history; 4) analyze changes or differences in the abundance of specific microbes or groups or divisions of microbes in the individual infant with respect to reference microbial profiles (established for the individual at an earlier time point or derived from the medical information of healthy infants); 5) provide an indicator to recommend treatments to change the microbial profile and achieve congruency with the selected reference microbial profile; and 6) periodically monitor the individual infant's microbial profile over time and recommend treatment when indicated.

Feces specimens collected from infant diapers are a ready source of intestinal microbes that are processed to identify and enumerate the bacterial classes, divisions and species inhabiting the lower intestine. To collect stool samples, sanitary napkins are placed in diapers (to prevent absorption of feces by the diaper), or feces tubes with a spoon (Sarstedt, Numbrecht, Germany) are used to obtain a standardized amount of material (see, for example, Penders et al, "Factors influencing the composition of intestinal micorbiota in early infancy," Pediatrics, 118: 511-521 (2006) which is incorporated herein by reference). Diapers suitable for stool collection may also be used, such as are described in U.S. Pat. No. 6,102,892 to Putzer, titled "Diaper with pleats for containment of liquid and solid waste," and U.S. Pat. No. 6,423,884 to Oehmen, titled "Absorbent article having apertures for fecal material," each of which is incorporated herein by reference. DNA for analysis is purified from feces specimens using a QIAamp DNA stool minikit (Qiagen, Hilden, Germany).

To determine the abundance of microbial species, quantitative real time polymerase chain reaction (PCR) is used. Quantitative analysis of bacterial species is performed using PCR amplification of genes encoding 16s ribosomal RNA (rRNA) using feces-derived genomic DNA as template and PCR primers specific for different bacterial species. Examples of primer sequences and reaction conditions are described in Ott et al, "Quantification of intestinal bacterial populations by real-time PCR with a universal primer set and minor groove binder probes: a global approach to the enteric flora," J. Clinical Microbiology, 42: 2566-2572 (2004) which is herein incorporated by reference. Using 96-well optical plates and an ABI Prism 7700 sequence detector (Applied Biosystems, Foster City, Calif.) (as shown by Ott et al, Ibid.) 16s ribosomal RNA genes are amplified with primers specific for bacterial species, group and genus, and intestinal flora are quantitated, with sensitivities ranging from 10 to 1000 bacterial cells. Exemplary data (from Ott et al, Ibid.) listing the number of *Bacteroides, Porphyromonas, and Prevotella* cells present in five clinical samples is shown in FIG. 12.

Figure 12:
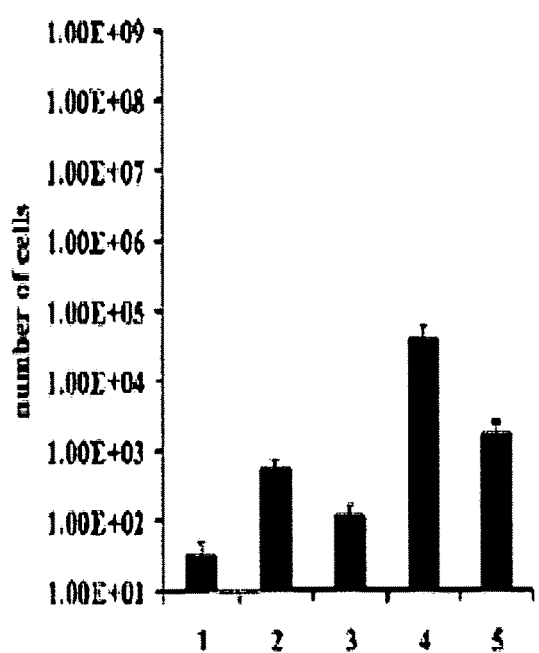
FIG. 12 depicts the number of cells detected by real-time PCR in clinical samples from five healthy control patients.

FIG. 12 depicts the number of cells detected by real-time PCR in clinical samples from five healthy control patients. Normalized mean values of two independent experiments±standard deviation. (Taken from Ott et al, Ibid.) *$C_T$=threshold cycle.

Alternatively or in addition to enumerate and identify classes, groups or species of infant intestinal microbes, stool samples are processed to obtain microbial DNA using established protocols and reagents (Qiagen Inc., Valencia, Calif.) and analyzed on microarrays. Microarrays containing probes for 16s rRNA genes that are specific for phyla, classes or species are constructed using the teachings of Palmer et al, "Development of the human infant intestinal microbiota," PLoS Biology, 5: 1556-1573 (2007) which is incorporated herein by reference. Microarrays with probes for 9121 unique taxonomically specific probes are constructed using 40 nucleotide sequences derived from 16s rRNA genes. The selection of 16s rRNA probe sequences and synthesizing surface-attached oligonucleotide probes in situ is as described (see Palmer et al, Ibid.). To interrogate microbial DNA derived from infant stool specimens, rRNA gene sequences are amplified using PCR using broad range bacterial primers that amplify more than 90% of bacterial 16s rRNA genes and also provide a promoter sequence for T7 RNA polymerase. Broad range bacterial-specific PCR primers, PCR reaction conditions and methods to purify amplified rDNA are as described in Palmer et al, Ibid. In vitro transcription with T7 polymerase, using the amplified bacterial rDNA as template, is used to prepare fluorescently-labeled RNA for hybridization to microarrays. Protocols and reagents for in vitro transcription and purification of RNA are available from Ambion, Inc., (Austin, Tex.). RNA is fluorescently-labeled with Cy5 using commercially available reagents and protocols (for example, the Minis Bio Label: Cy5 Labeling Kit available from Fisher Scientific, Pittsburgh, Pa.). Reaction conditions for hybridization of fluorescently-labeled RNA to microarrays are as described in Palmer et al, Ibid. Equipment and instruments for hybridization and analysis of microarrays are available from Agilent Technologies, Inc., (Santa Clara, Calif.).

Information obtained using microarrays or quantitative PCR (as described above) is incorporated into a profile of intestinal microbe abundance and integrated with medical data for each infant. A system that integrates an infant's microbial profile with, for example, factors such as gestational age, route of delivery (vaginal or Caesarian section), weight, nutrition, diet, antibiotic use, drug use, viral (e.g. HIV) or bacterial exposure, genotype, epigenetics and family history is used to associate environmental, genetic, epigenetic and medical factors with microbial diversity and abundance. For example, as shown by Penders et al, Ibid., using multivariate analysis "beneficial microbes" (e.g. *bifidobacteria* and *Bacteroides*) are identifiable that associate with full-term infants, and the factors of breast feeding and vaginal birth. An example, (taken from Penders et al, Ibid.) of linear regression analysis that associates microbial numbers with medical data is shown in FIG. 13. FIG. 13 depicts linear regression coefficients for bacterial counts and odds ratios for the presence of gut bacteria, with respect to determinants in multivariate analyses. Coefficients are regression coefficients of association between determinants and counts, determined with linear regression analyses. Odds ratios (ORs) of association between determinants and prevalence of colonization (colonized compared with not colonized) are determined with logistic regression analyses. ND indicates not determined (logistic regression analysis of prevalence of *bifidobacteria* was not performed because 99% of infants were colonized). Adapted from Penders et al, Ibid. *Statistically significant results (at P=0.01, 2-sided). Moreover, analysis of medical data such as on antibiotic use, prematurity and hospitalization shows associations with specific potential pathogens such as *Clostridium difficile* and *E. coli* (see Penders et al, Ibid.).

To establish a reference microbial profile, the microbial profile for a number (e.g. 14-1000) of healthy infants is determined. Information from these microbial profiles is then used to generate a standard microbial profile for healthy infants. Integration of microbial profiles and medical data allows for the calculation of microbial profiles whose microbial diversity and abundance associate with healthy infants displaying normal weight gain, digestion and clinical parameters relating to health and illness. For example, a "healthy" intestinal microbial profile is delineated at the level of prokaryotic phyla by analysis of stool samples from healthy infants. For example, Palmer et al, Ibid. have observed a "preponderance of *Bacteroides* and Firmicutes, common occurrence of Verrucomicrobia, and very low abundance of Proteobacteria and aerobic Gram-negative bacteria in general."

Alternatively or in addition, a reference microbial profile is established for an infant by integrating medical data and a microbial profile observed at a first time point. Data from stool samples collected and analyzed at later time points are compared to the initial reference microbial profile. Stool samples collected at birth and then at later time points such as daily, weekly and monthly are used to analyze the temporal development of microbial flora following birth (for example, see Palmer et al, Ibid.). Integration of medical data obtained at the time of each sampling allows for the association of factors such as therapies, medical procedures, illnesses, infections, diet and environmental, genetic, epigenetic and other factors with microbial abundance and diversity over time. For example, changes in the density and composition of intestinal microbes are associated with antibiotic administration. Microbial profiling of an infant treated with amoxicillin at 4 months of age detects a decrease in total bacterial density and altered bacterial composition in stool samples relative to a reference microbial profile established at 1 month of age as shown by Palmer et al, Ibid. Also amoxicillin treatment is associated with changes in the abundance of specific bacterial groups, for example, reductions in gamma proteobacteria, and increases in *bacilli* as shown by Palmer et al, Ibid.

Figure 14:
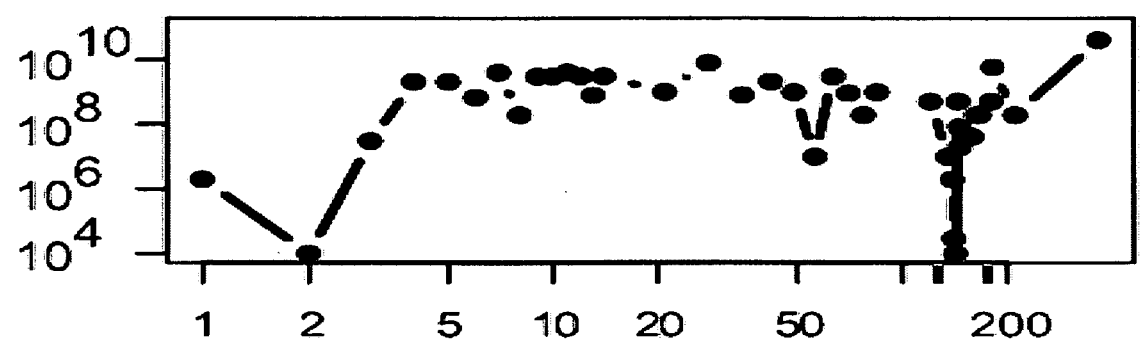
FIG. 14 depicts variation in total fecal bacterial density and specific taxa for an infant treated with antibiotics.

FIG. 14 depicts variation in total fecal bacterial density and specific taxa for an infant treated with antibiotics. Taken from Palmer et al, Ibid. Estimated rRNA gene copies per gram of feces (y-axis) are plotted as a function of days of life (x-axis). Both axes are on a logarithmic scale. Episodes of antibacterial treatment are indicated on the temporal axis by gray bars. Within a few days of the antibiotic treatment, a sharp increase in the levels of *Bacteroides* and *Cytophaga* were observed (from less than 40 rRNA gene copies per gram of feces to over 80 rRNA gene copies per gram). Similarly, levels of *Bacilli* and related species sharply increased during the time of antibiotic treatment, from a pre-treatment low of negligible levels to a high of over 60 rRNA gene copies per gram of feces. After antibiotic treatment, the levels of *Bacilli* and related species returned to negligible levels. However, levels of *Clostridia* and related species, which had been negligible or under 20 rRNA gene copies per gram of feces from birth until the time of antibiotic treatment, increased after antibiotic treatment to approximately 20 rRNA gene copies per gram of feces and maintained this increase for the duration of the study period. Systems as those described herein monitor such post-antibiotic use increases in specific pathogen species or classes and suggest interventions to improve health after the end of an antibiotic course.

To modify an infant's microbial profile, the system suggests treatments to increase or decrease specific divisions, classes or species of intestinal microbes. For example, infants treated with antibiotics display reduced numbers of *bifidobacteria* and *Bacteroides* (see Penders et al, Ibid.). One potential recommended treatment is administration of in vitro cultures of *Bacteroides* and *bifidobacteria* (obtained from healthy, untreated infant feces) and reconstituted with saline to be administered using an enema or by colonoscope. A potential treatment includes liquid cultures of *Bacteroides* and *bifidobacteria* lyophilized and reconstituted in appropriate diluent before enteric or colonic administration, as described in U.S. Pat. No. 6,645,530 to Borody titled "Treatment of gastro-intestinal disorders," which is incorporated herein by reference. In addition, recommended treatments include prebiotics which promote the growth of specific groups of bacteria. For example, to promote the growth of *bifidobacteria*, prebiotics such as fructooligosaccharides, inulin, soybean oligosaccharides, and transgalactosylated oligosaccharides are administered orally. See, for example, Schrezenmeir et al, "Probiotics, prebiotics, and synbiotics—approaching a definition," Am. J. Clin. Nutr., 73 (suppl): 361S-364S (2001) and U.S. Pat. No. 6,706,287 to Ranganathan et al. titled "Prebiotic and probiotic compositions and methods for their use in gut-based therapies," which are herein incorporated by reference.

To reduce the number of undesirable or pathogenic bacteria, treatment with antibacterials are suggested. For example, lytic bacteriophage are isolated and propagated in vitro that are suitable for treating pediatric gastroenteritis. "T4-like" bacteriophage with a broad host range for pathogenic *E. coli* and *Salmonella* are propagated, purified and given orally to infants in infant formula. See, for example, U.S. Pat. No. 7,211,426 to Bruessow et al. titled "Isolated phages and their use in food or pet food products," which is herein incorporated by reference. Methods and compositions for propagating, isolating, purifying, formulating and administering "T4-like" bacteriophage with lytic activity for pathogenic *E. coli* and *Salmonella* are described in U.S. Pat. No. 7,211,426, to Bruessow et al. titled "Isolated phages and their use in food or pet food products," which is herein incorporated by reference. Alternatively or in addition, antibacterial treatment includes antimicrobial peptides, such as those described in U.S. Patent Application No. 2008/0170991 to Shi et al., titled "Selectively targeted antimicrobial peptides and the use thereof," which is incorporated herein by reference. For example, andropin, apidaecin, bactencin, clavanin, dodecappeptide, defensin, and indolicidin are antimicrobial peptides having antibacterial activities. Also tachyplesins are known to have antifungal and antibacterial activities. Buforin, nisin and cecropin peptides have antimicrobial effects on *Escherichia coli, Shigella disenteriae, Salmonella typhimurium, Streptococcus pneumoniae, Staphylococcus aureus*, and *Pseudomonas aeruginosa*. Magainin and ranalexin peptides have antimicrobial effects on the same organisms, and in addition have such effects on *Candida albicans, Cryptococcus neoformans, Candida krusei*, and *Helicobacter pylori*. Alexomycin peptides have antimicrobial effects on *Campylobacter jejuni, Moraxella catarrhalis* and *Haemophilus influenzae*, while defensin and .beta.-pleated sheet defensin peptides have antimicrobial effects on *Streptococcus pneumoniae*. Antimicrobial peptides are fused to targeting peptides to create antimicrobials with specificity for microbial pathogens that spare beneficial gut microbes. Methods for creating targeted antimicrobial peptides are described in U.S. Patent Application No. 20080170991, to Shi et al., titled "Selectively targeted antimicrobial peptides and the use thereof," which is incorporated herein by reference. Following suggestions for the treatment of infants to modify their microbial profile, the system periodically monitors their microbial flora and analyzes changes in microbial profiles, and may recommend additional treatment for restoration or establishment of a beneficial microbial composition.

Example 2

A system that analyzes, identifies and lists changes in a patient's microbiome or microbial profile, with respect to a reference microbial profile, indicates potential treatments to promote cardiovascular health. Some possible treatment suggestions are: nutritional changes, probiotics, prebiotics, synbiotics, enzymes, bacterial phyla, bacterial species, fungal species, therapeutics, antifungals, antibacterials, antimicrobials, and antibiotics. Patients with specific microbial profiles are at increased risk for cardiovascular disease, and treatment suggestions are indicated in regard to such patients by a system that compares a patient's microbial profile to one or more reference microbial profiles derived from information associated with individuals in good cardiovascular health. Reference microbial profiles relative to cardiovascular health, for example, integrate factors such as plasma ferulic acid levels, plasma C-reactive protein levels, and plasma lipid levels. The system lists, for example, differences in intestinal microbial diversity and abundance. The system evaluates and indicates a need for treatment, and recommends a treatment such as a prebiotic to modify the microbial profile. For example, where indicated the system suggests treatment of intestinal microbiota with a prebiotic, such as enzymatically-digested durum wheat fiber, to modify the numbers of specific microbiota groups (e.g. *bifidobacteria* and *lactobacilli*) and result in the increased release of the antioxidant ferulic acid, which has been suggested to promote cardiovascular health. See Napolitano et al, "Potential prebiotic activity of oligosaccharides obtained by enzymatic conversion of durum wheat insoluble dietary fibre into soluble dietary fibre," Nutrition, Metabolism Cardiovascular Diseases (2008), in press, available online as of 20 Sep. 2008, DOI: 10.1016/j.numecd.2008.07.005, which is herein incorporated by reference. Alternatively or in addition, a system may recommend a synbiotic comprised of a prebiotic (e.g. oligofructose, enzyme-digested durum wheat fiber) and a probiotic (e.g. *bifidobacteria* such as *B. adolescentis, B. animalis* spp. lactis, *B. breve, B. longum*) (see Schrezenmeir et al, et al, "Probiotics, prebiotics, and synbiotics—approaching a definition," Am. J. Clin. Nutr., 73 (suppl): 361S-364S (2001), which is herein incorporated by reference). In addition, repeated determinations of patient microbial profiles pre- and post-treatment are compared to at least one reference microbial profile and analyzed with respect to time in order to monitor modifications to microbial abundance and diversity over time, such as in response to one or more therapies. The system also continuously monitors microbial profiles including parameters of cardiovascular health, and calculates and lists differences in comparison to a reference microbial profile. Periodically, the system may indicate a need for treatment and recommend the dispensation of a treatment, for example a prebiotic such as enzyme-digested wheat fiber.

A system for monitoring microbial profiles and integrating data (e.g. diet, microbial exposure from food, digestion, regularity of bowel movements, and metabolic parameters such as blood glucose levels and insulin levels) into individual profiles indicates potential adverse changes in intestinal microbial composition and makes dietary recommendations to restore microbial compositions and promote health. To monitor the intestinal microbial flora, bacterial cellular fatty acids are extracted from stool samples and analyzed using gas-liquid chromatography (GLC). Fatty acid GLC profiles are used to represent the microbial flora present in the stool samples and allow for the detection of differences or changes in the microbial flora of individuals or groups. Initially, bacteria present in stool samples are isolated by sedimentation and centrifugation to yield a bacterial pellet. Prior to GLC, the bacterial samples are saponified, methylated and extracted to isolate fatty acids. See, Peltonen et al, "An uncooked vegan diet shifts the profile of human fecal microflora: computerized analysis of direct stool sample gas-liquid chromatography profiles of bacterial cellular fatty acids," Applied Environmental Microbiology, 58:3660-3666 (1992) which is herein incorporated by reference. GLC is performed with a gas chromatograph (such as those available from Thermo Fisher Scientific, Inc., Waltham, Mass.). Detailed protocols and materials for GLC analysis of fatty acids from fecal bacteria are described in Peltonen et al, Ibid. GLC data analysis of stool specimens are based on GLC spectra from bacterial species analyzed in isolation. Computer analysis allows calculation of similarity indices for each pair of samples; in addition mean indices for sample groups are calculated to allow comparison of test groups or control groups. For example, one can detect significant changes in mean fatty acid similarity indices for a test group fed an uncooked vegan diet when compared to a control group fed an omnivorous Western diet. See FIG. 15, taken from Peltonen et al, Ibid. Data on microbial flora, as indicated by fatty acid profiles and similarity indices, is integrated with medical data to indicate changes associated with health and disease and diet. Microbial profiles associated with disease and poor health are used to indicate a need for treatment and to recommend dietary changes to modify microbial profiles to benefit health.

Figure 15:
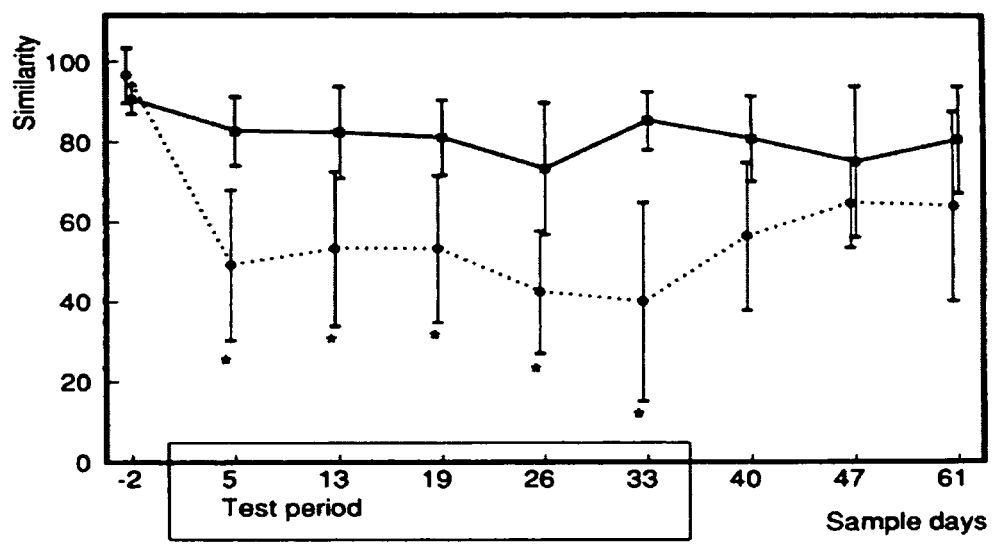
FIG. 15 illustrates changes in microbial profiles in individuals consuming different diets over time.

FIG. 15 shows that a vegan diet alters fecal microflora as measured by GLC fatty acid profile analysis. The mean value of similarity indices (±standard deviation) are calculated by comparison to pretest profiles for control group (squares, solid line) and vegan diet group (circles, dotted line). * indicates statistically significant (P<0.05) difference from pretest profiles and from control group samples collected on the same day. Taken from Peltonen et al, Ibid.

A system that integrates microbial profiles, metabolic data, medical data, genetics and diet indicates desirable alterations in diet and recommends appropriate treatments to modify microbial profiles. By integrating data regarding metabolites present in plasma and urine with other medical data relating to individuals, cometabolites (i.e. metabolites arising from the combined action of host and commensal microbe metabolism) are associated with disease states. See, for example, Dumas et al, "Metabolic profiling reveals a contribution of gut microbiota to fatty liver phenotype in insulin-resistant mice," Proc. Natl. Acad. Sci. USA, 103: 12511-12516 (2006) which is herein incorporated by reference. Using $^1$H nuclear magnetic resonance (NMR) spectroscopy and multivariate statistical modeling, Dumas et al, Ibid. shows that impaired glucose homeostasis and nonalcoholic fatty liver disease (NAFLD) induced by a high-fat diet in mouse strain 129S6 are associated with disruptions of choline metabolism. Specifically, low circulating levels of plasma phosphatidylcholine and high urinary secretion of methylamines, cometabolites of choline resulting from gut microbe processing, are associated with NAFLD and insulin resistance (see Dumas et al, Ibid.). Data from glucose tolerance testing, insulin secretion studies, liver histopathology, liver triglyceride testing, plasma aspartate aminotransferase testing, and plasma alanine aminotransferase testing shows that a high fat diet induces NAFLD, impaired glucose tolerance, and dyslipidemia in 129S6 mice but not in Balb/c control mice. As shown by Dumas et al, Ibid., $^1$H NMR analysis of plasma samples from 129S6 mice fed a high-fat diet indicates a reduction in phosphatidyl choline and a significant increase in microbiota-derived methylamines including dimethylamine, trimethylamine and trimethylamine-N-oxide.

Systems and methods such as those described herein integrate data regarding microbial profiles associated with urinary metabolites with metabolite data and medical data from specific individuals and list differences between control (i.e. healthy) subjects and patients. Metabolic indicators of impaired glucose metabolism or NAFLD are possible factors leading to the suggestion of specific treatments. For example, an individual exhibiting elevated urinary methylamines and reduced plasma PC is indicated as at risk for NAFLD and recommended treatments include a low fat diet as well as modification of the individual's microbial profile.

Example 3

A microbial monitoring system is used to identify and recommend treatments for genetic diseases such as Familial Mediterranean Fever (FMF). FMF is caused by mutations in a single gene, MEFV (Mediterranean Fever), that encodes a protein, pyrin, which is involved in regulating innate immunity and inflammation. A gastrointestinal microbial profile that integrates an individual's genotype for MEFV with clinical symptoms of FMF, including markers of remission and attack, is used to identify microbial imbalances associated with FMF symptoms and to recommend treatments to modify microbial profiles and reduce inflammation in individual FMF patients. Profiles of gastrointestinal microbial diversity and abundance are determined for clinically diagnosed FMF patients as well as for healthy volunteers that are matched with respect to ethnic information associated with the patients and volunteers in a personal information database.

To evaluate microbial diversity and abundance, microbial 16s ribosomal DNA (rDNA) sequences are determined from gastrointestinal samples taken from individual patients and volunteers. Fecal samples are extracted to obtain microbial genomic DNA (methods and reagents from Qiagen, Inc., Valencia, Calif.). Microbial 16s ribosomal RNA (rRNA)

gene fragments are amplified from the extracted DNA using polymerase chain reaction (PCR) and universal primers for microbial 16s rRNA genes as described in Khachatryan et al, "Predominant role of host genetics in controlling the composition of gut microbiota," PLoS ONE, 3:e3064 (2008) which is herein incorporated by reference. Amplified 16s rDNA fragments are isolated, purified and cloned in a plasmid vector such as pCR-4 in *E. coli* TOP 10 (available from Invitrogen Corp., Carlsbad, Calif.). The library of cloned 16s rDNA fragments is sequenced using an automated capillary sequencer (Beckman Instruments, Fullerton, Calif.) and the rDNA sequences aligned, edited, and evaluated for similarity and phylogenetics using bioinformatics programs such as CLUSTALX, BLAST, DNADIST, DOTUR and RDP-II (see Khachatryan et al, Ibid. for more information regarding these programs).

Systems comparing 16s rDNA libraries from healthy controls and FMF patients (in remission or attack) indicate differences in microbial composition between healthy individuals and FMF individuals. For example, FIG. 16 illustrates the comparison of 16S rRNA gene libraries derived from healthy controls and FMF patients in remission and attack. (* p,0.01, comparison of remission vs. control libraries.  p,0.01, comparison of attack vs. control libraries. * p,0.01, comparison of remission vs. attack libraries.) Data shown in FIG. 16 taken from Khachatryan et al, "Predominant role of host genetics in controlling the composition of gut microbiota," PLoS ONE, 3:e3064 (2008) which is herein incorporated by reference. As indicated by the data presented in FIG. 16, in asymptomatic FMF patients in remission, the proportion of *Enterobacteriaceae, Acidaminococcaceae, Ruminococcus* and *Megasphaera* is significantly increased in comparison with control subjects, while *Roseburia* is significantly reduced. In FMF patients with active disease, the percentages of *Porphyromonadaceae Phascolarctobacterium, Faecalibacterium*, and *Parabacteroides* are increased relative to control subjects, and the percentages of *Prevotellaceae, Dialister* and *Prevotella* are decreased. Another approach to generating microbial profiles is using fluorescent in situ hybridization (FISH) to identify and enumerate fecal bacteria. Microbial profiles based on FISH results may augment those obtained by cloning and sequencing (as above) or FISH-based data may be used to generate profiles independently. The predominant groups of bacteria in fecal samples are quantified using Cy3-labelled oligonucleotide probes for 16s rRNA genes hybridized to bacterial DNA in cells fixed on microscope slides to generate FISH data. Hybridization in bacterial cells is counted automatically using image analysis software, such as with Quantimet HR600 and a Leica DMRXA epifluorescence microscope (Wetzlar, Germany). Detailed methods and materials including Cy3-labeled oligonucleotide probes, hybridization conditions, preparation of fixed bacteria on microscope slides and data analysis techniques are described in Khachatryan et al, Ibid. Microbial profiles from fecal specimens derived from healthy controls and patients with genetic diseases such as FMF are based on data generated using techniques including FISH and DNA sequencing of 16s rDNA libraries.

To create an informative reference microbial profile and to associate microbial profiles with genetic disease information, a microbial monitoring system incorporates genetic data from individuals. For example, an individual's genotype, including alleles, cDNA or gDNA sequence, for MEFV is determined using PCR amplification and sequencing of gDNA or cDNA derived from blood or tissue samples. Where such testing has been done previously, an individual's genotype may also be obtained from information existing as part of an individual's medical record. Genomic DNA and RNA are isolated from blood or tissue samples using reagents and protocols available from Qiagen Inc., (Valencia, Calif.). The FlexiGene DNA kit is used for samples of whole blood between 1 and 5 mL, while the DNeasy Blood and Tissue Kit is used for tissue or smaller blood volumes (Qiagen Inc., Valencia, Calif.). PCR primers and reaction conditions specific for exon 10 and exon 2 (the sites of known mutations) of the MEFV gene are as described in Khachatryan et al, Ibid. PCR-amplified fragments from the MEFV gene are purified using Qiagen reagents and sequenced using an automated capillary DNA sequencer (Beckman Instruments Inc., Fullerton, Calif.).

Information regarding mutations in the MEFV gene of specific individuals relative to sequences derived from healthy control subjects is incorporated into a microbial reference profile and represented to a system user as particular combinations of alleles, including heterozygous or homozygous mutations. The system also accepts medical data relating to inflammatory symptoms such as fever, influx of polymorphonuclear leukocytes, neutrophilia, and acute-phase response. In addition, clinical data such as blood levels of C-reactive protein, SAA, and interferon gamma are integrated into individual profiles.

A microbial monitoring system is used to profile subjects who are suspected to have FMF in addition to profiling known FMF patients. For example, the system is used generate microbial profiles for individuals exhibiting clinical symptoms of FMF (e.g. repeated episodes of fever and polyseritis) but lacking genotype information and specific diagnosis, or individuals that are related to an MEFV carrier or an FMF patient but have displayed inconclusive symptoms. Individuals who have tested positive for a mutant MEFV gene allele but do not display clinical symptoms are also profiled. A system that integrates clinical and genotype information with microbial diversity and abundance data assists caregivers in diagnosing FMF and also indicates potential treatments and recommends treatments. For example, a fecal microbial profile associated with FMF patients during attack (i.e. fever and inflammation) displays low proportions of the bacterial taxa *Prevotellaceae, Dialister* and *Prevotella* relative to healthy control subjects (see FIG. 16 and Khachatryan et al, Ibid.). Identification of such a microbial profile in a patient suspected of having FMF in conjunction with genotype and clinical information increases confidence in the diagnosis of FMF and assists in suggesting appropriate treatments for FMF in individual patients. A system may suggest treatment including a probiotic containing the depleted bacteria *Prevotellaceae, Dialister* and *Prevotella* in the appropriate proportions to be administered orally along with anti-inflammatory drugs such as aspirin and acetaminophen. There is increased confidence in diagnosis when suspected FMF patients display a microbial profile associated with FMF patients, and furthermore can facilitate treatment at the time of future acute episodes. FMF patients in remission display a microbial profile with increased proportions of *Enterobacteriaceae, Acidaminococcaceae, Ruminococcus* and *Megasphaera* in comparison with control subjects, while *Roseburia* is significantly reduced (see FIG. 16 and Khachatryan et al, Ibid.). For suspected FMF patients, a microbial monitoring system integrates genotypic data, clinical data, family history and at least one microbial profile to assist medical personnel in the diagnosis and effective treatment of FMF. For example, any specific bacterial species that are overrepresented in FMF individuals may be targeted with antibacterial agents.

Example 4

A microbial monitoring system assists in the evaluation and treatment of elderly patients and travelers exposed to new environmental microbial flora. The system assists individuals and health care professionals to make informed decisions regarding possible interventions to improve the health of immigrants. Genetics, age, environment, diet and drugs are important determinants of the microbial composition of gut flora in healthy and diseased individuals. Individuals who have recently moved into a new environment (for example, elderly immigrants, such as parents or grandparents of Chinese-Americans, Japanese-Americans and Latin-Americans) benefit from a system which monitors microbial flora and recommends treatments to improve health in the new locale. For example, an elderly immigrant will benefit from modification of his or her gastrointestinal microbial profile to align it with a reference profile based on data from individuals of a similar ethnic background who have been living in the new locale for some time or to maintain their original profile in spite of the change in the diet. Microbial samples from the gastrointestinal tract are obtained using an ingested sampling device (see, for example, U.S. patent application to Boyden et al., titled "Adaptive dispensation in a digestive tract, filed on Oct. 23, 2007 and US Patent Application No. 2009/0112191 to Boyden et al. titled "Medical or veterinary digestive tract utilization systems and methods" which are herein incorporated by reference). Alternatively or in addition, samples from the digestive tract are obtained with an endoscopic device. The choice of sampling method for any individual patient may depend on personal choice of the medical staff relative to other medical indications, or the needs and preferences of the individual patient. Analysis of microbial diversity and abundance may be made using DNA sequencing of 16s rDNA clone libraries (as above).

Analysis of microbial diversity and abundance may also be generated using denaturing gradient gel electrophoresis (DGGE) data integrated into the systems and methods described herein. For example, DGGE analysis of fecal samples from a Chinese family has reveals differences in microbial composition at the species level relative to American individuals (see Li et al, "Symbiotic gut microbes modulate human metabolic phenotypes," Proc. Natl. Acad. Sci. USA, 105: 2117-2122 (2008), which is herein incorporated by reference).

In addition, microbial monitoring of single individuals over time indicates the stability of an individual's microbial profile over time, or changes that may result from a new environment, new diet or ageing (see Li et al, Ibid.). For example, travelers from industrialized nations to tropical developing countries contract traveler's diarrhea that is associated with enteric microbial pathogens, and it has been noted that "approximately 80% of traveler's diarrhea cases with an identified pathogen are caused by bacteria, including enterotoxigenic *Escherichia coli* (ETEC), recently identified enteroaggregative *E. coli* (EAEC), *Salmonella* spp., *Shigella* spp., *Campylobacter* spp., *Plesiomonas shigelloides, Aeromonas* spp., and non-cholera-causing vibrios" (quoted from Gomi et al, "In vitro antimicrobial susceptibility testing of bacterial enteropathogens causing traveler's diarrhea in four geographic regions," Antimicrobial Agents and Chemotherapy, 45: 212-216 (2001) which is herein incorporated by reference).

A microbial monitoring system accepts data on the abundance of bacterial pathogens such as enterotoxigenic *Escherichia coli* (ETEC) and enteroaggregative *E. coli* (EAEC) (see Gomi et al, Ibid. for methods), and integrates data on the susceptibility of microbial pathogens to antimicrobials such as ampicillin (AMP; Sigma Chemical Co., St. Louis, Mo.), trimethoprim (TMP; Sigma), TMP/sulfamethoxazole (SXT; Sigma), doxycycline (DOX; Sigma), nalidixic acid (NAL; Sigma), amdinocillin (MEC; Leo Pharmaceutical Products, Copenhagen, Denmark), ceftriaxone (CRO; Sigma), ciprofloxacin (CIP; Medlatech Inc., Herndon, Va.), levofloxacin (LVX; Pharmaceutical Research Institute, Spring House, Pa.), azithromycin (AZM; Pfizer Inc., Brooklyn, N.Y.), and rifaximin (RFX; Alfa Wassermann, Bologna, Italy). Such integrated data is used by the system to suggest treatments specific to individuals based on their profiles.

The susceptibility of bacterial pathogens associated with traveler's diarrhea to antibiotics is shown in FIG. 17. FIG. 17 depicts the minimum inhibitory concentration (MIC) of antimicrobials for enteropathogens at the $MIC_{90}$ level. Table reference (a) denotes $MIC_{90}$, which is the MIC required to inhibit the growth of 90% of the strains tested. Table reference (b) indicates that data for CRO and AZM are based on 268 pathogens. Table reference (c) indicates that the column headed "Others" denotes other pathogens, including non-cholera-causing vibrios, *P. shigelloides*, and *Aeromonas* sp. Isolates. Taken from Gomi et al, Ibid.

A microbial monitoring system indicates when treatment is needed and recommends treatments to caregivers and individuals. For example, a patient with an ETEC infection is indicated as potentially benefitting from treatment and the system recommends AZM or CIP or CRO based on the MIC values for these antimicrobials (see FIG. 17). Conversely, AMP, TMP and SXT would be disfavored due to their high MIC values as extremely high doses of antibiotics are generally less medically desirable treatments. Such antibiotics are suggested with an indication of high dosages needed relative to the MIC levels for specific pathogens so that a healthcare professional may make a final treatment choice. The system also integrates data regarding an individual's complete intestinal microbial profile and medical data such as age, existing diseases, antibiotic allergies, and current medications to indicate and recommend treatments for traveler's diarrhea and other enteric microbial diseases. Repeated microbial profiling is used to monitor an individual's health over time and evaluate treatment efficacy. For example, changes in microbial profile, especially changes in abundance of enteropathogens and a reduction in normal microbial flora resulting from antimicrobial treatment, indicates a need for further treatment and/or alternate treatments such as different antimicrobials or probiotics to restore a normal microbial flora balance.

Elderly individuals often display changes in the composition of their microbial flora that can directly cause disease or make them susceptible to disease. A microbial monitoring system that accepts and integrates data on age, microbial composition and abundance, antibiotic use and environmental data is used to detect and indicate changes in gastrointestinal microbial flora and to recommend treatments to rebalance the microbiota of elderly individuals. Ageing is generally accompanied by changes in an individual's gastrointestinal tract as well as in their diet and immune system responses. For example, ageing is associated with increased numbers of facultative anaerobes and decreased numbers of beneficial anaerobes such as *bifidobacteria* and *lactobacilli* as well as a general reduction in the species diversity for most bacterial groups (see, for example, Woodmansey et al, "Intestinal bacteria and aging," J. Appl. Microb., 102: 1178-1186 (2007), which is herein incorporated by reference).

Ageing individuals often display decreased intestinal motility and consequent increased intestinal transit times that can make them more susceptible to disease. Decreased numbers of *Bacteroides* are associated with increased age and this is magnified following antibiotic therapy. Species diversity within *Bacteroides* is also often reduced in the elderly. Changes in *Bacteroides* abundance and diversity correlates with a reduction in amylolitic activity (Woodmansey et al, Ibid.), and microbial profiles with reduced numbers of *Bacteroides* are associated with obesity, which is undesirable at any age (see Ley et al, "Human gut microbes associated with obesity," Nature 444: 1022-1023 (2006) which is herein incorporated by reference). Furthermore, elderly individuals often display increased intestinal proteolytic activity associated with increased numbers of *Fusobacteria, Propionibacteria* and *Clostridia*. Elderly individuals treated with antibiotics display increased abundance and diversity of *clostridia* species including: *Clostridium bifermentans, Clostridium clostridioforme, Clostridium sordellii* and *Clostridium malenominatum* and the pathogen *Clostridium difficile* (Woodmansey et al, Ibid.). Yet the abundance and diversity of beneficial *Bifidobacteria* tend to be reduced in elderly individuals, so that frequently only a few species remain, for example, *Bifidobacterium adolescentis, Bifidobacterium angulatum*, and *Bifidobacterium longum* (Woodmansey et al, Ibid.).

A system monitoring the changes in microbial abundance and diversity with age to detect and indicate changes in the abundance of bacterial divisions and the diversity of bacterial species which accompany the ageing process also suggests interventions to modify these effects. Reference microbial profiles established, for example, with samples and medical data from healthy elderly subjects, younger individuals, sick elderly patients, patients receiving antibiotics and data from the biomedical literature are used to analyze changes and recommend treatments. As with all systems described herein, the choice of appropriate reference profile individuals and data is at the option of the system user and/or programmer. Elderly patients may be sampled periodically such as annually, semi-annually, monthly or weekly to establish a reference microbial profile from a particular individual that can be used for difference analysis. Microbial samples may be taken during regular medical events such as check-ups or evaluations. A microbial profile system recommends treatments as indicated to restore a healthy microbial profile or to eliminate microbial pathogens. For example, reduced beneficial bacteria such as *Bifidobacteria* may be supplemented with probiotics (e.g. *Bifidobacterium bifidum* and *Bifidobacterium longum*) and prebiotics (e.g. oligofructose) to specifically increase their abundance and promote diversity (Woodmansey et al, Ibid.). In situations wherein the microbial profile system detects a bacterial pathogen such as *C. difficile*, or indicates a significant change in *C. difficile* abundance, they system recommends treatment with probiotics such as *Lactobacillus plantarum* and *B. bifidum* combined with prebiotics such as fructooligosaccharides, inulin and xylooligosaccharides (Woodmansey et al, Ibid.).

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. For example, those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation)

may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A system for continual modification of intestinal microbes comprising:
at least one ingestible sampling device including one or more electronic detectors, the at least one ingestible sampling device including one or more physical sample collectors and an internal storage region;

at least one analysis device including a cell culture of the at least one sample;

at least one computational device operably connected to the at least one analysis device, and including in memory a standard profile for gastrointestinal microbes;

at least one user interface device operably connected to the at least one computational device, the user interface device including a monitor; and at least one material dispensing device connected to the at least one computational device.

2. The system of claim 1, wherein the at least one sampling device comprises:
one or more chemical sensors.

3. The system of claim 1, wherein the at least one sampling device comprises:
one or more containers.

4. The system of claim 1, wherein the at least one sampling device comprises:
one or more absorbent pads.

5. The system of claim 1, wherein the at least one sampling device comprises:
at least one additional ingestible sampling device.

6. The system of claim 1, wherein the at least one analysis device comprises:
at least one nucleic acid analysis device.

7. The system of claim 1, wherein the at least one analysis device comprises:
at least one protein analysis device.

8. The system of claim 1, wherein the at least one analysis device comprises:
at least one chemical analysis device.

9. The system of claim 1, wherein the at least one analysis device comprises:
at least one electronic detectors.

10. The system of claim 1, wherein the at least one computational device and the at least one user interface device are an integrated unit.

11. The system of claim 1, comprising:
at least one additional sampling device.

12. The system of claim 1, comprising:
at least one dietary sampling device.

13. The system of claim 12, wherein the at least one dietary sampling device is operably connected to the at least one computational device.

14. A system for monitoring and introducing gastrointestinal microbes into a mammalian gastrointestinal tract over time, comprising:

at least one gastrointestinal microbe analysis device;

at least one computational device connected to the at least one gastrointestinal microbe analysis device, the at least one computational device including logic with protocols to integrate information relating to an individual with information from the at least one gastrointestinal microbe analysis device;

at least one user interface connected to the at least one computational device; and at least one material dispensing device connected to the at least one computational device, the at least one material dispensing device including control circuitry for the at least one material dispensing device and at least one data storage unit including dispensation protocols.

15. The system of claim 14, wherein the at least one gastrointestinal microbe analysis device is configured to be reusable.

16. The system of claim 14, wherein the at least one gastrointestinal microbe analysis device comprises:
at least one nucleic acid analysis device.

17. The system of claim 14, wherein the at least one gastrointestinal microbe analysis device comprises:
at least one protein analysis device.

18. The system of claim 14, wherein the at least one gastrointestinal microbe analysis device comprises:
at least one chemical analysis device.

19. The system of claim 14, wherein the at least one gastrointestinal microbe analysis device includes an electronic detector.

20. The system of claim 14, wherein the at least one computational device is connected to the at least one gastrointestinal microbe analysis device.

21. The system of claim 14, wherein the at least one material dispensing device is configured to dispense at least one microbe, antibiotic, antifungal, prebiotic, or probiotic agent.

22. The system of claim 14, comprising:
at least one additional gastrointestinal microbe analysis device.

23. The system of claim 14, comprising:
at least one dietary sampling device.

24. The system of claim 23, wherein the at least one dietary sampling device is operably connected to the at least one computational device.

* * * * *